United States Patent [19]

Haines

[11] 4,175,135
[45] Nov. 20, 1979

[54] METHOD OF CONTROLLING ACARINA ECTOPARASITES ON WARMBLOODED ANIMALS BY ORALLY ADMINISTERING TO THE ANIMAL AN ECTOPARASITICALLY EFFECTIVE AMOUNT OF A 2-ARYL-1,3-CYCLOHEXANEDIONE COMPOUND, AND ALKALI METAL SALTS, AMMONIUM SALTS AND ENOL ESTERS THEREOF

[75] Inventor: Robert G. Haines, Orange Park, Fla.

[73] Assignee: Union Carbide Corporation, New York, N.Y.

[21] Appl. No.: 925,814

[22] Filed: Jul. 18, 1978

[51] Int. Cl.² .................... A61K 31/22; A61K 31/12; A61K 31/275

[52] U.S. Cl. .................... 424/311; 424/304; 424/305; 424/308; 424/309; 424/312; 424/314; 424/324; 424/330; 424/331

[58] Field of Search ............... 424/331, 304, 324, 330, 424/305, 308, 311, 309, 312, 314; 260/590 C

[56] References Cited

U.S. PATENT DOCUMENTS

| 3,879,468 | 4/1975 | Durden | 424/331 |
|---|---|---|---|
| 3,927,207 | 12/1975 | Francke et al. | 424/331 |

*Primary Examiner*—Sam Rosen
*Attorney, Agent, or Firm*—Clement J. Vicari

[57] ABSTRACT

A method of controlling acarina ectoparasites on warmblooded animals by orally administering to the animals an ectoparasitically effective amount of a 2-aryl-1,3-cyclohexanedione compound and alkali metal salts, ammonium salts and enol ester derivative thereof.

11 Claims, No Drawings

METHOD OF CONTROLLING ACARINA ECTOPARASITES ON WARMBLOODED ANIMALS BY ORALLY ADMINISTERING TO THE ANIMAL AN ECTOPARASITICALLY EFFECTIVE AMOUNT OF A 2-ARYL-1,3-CYCLOHEXANEDIONE COMPOUND, AND ALKALI METAL SALTS, AMMONIUM SALTS AND ENOL ESTERS THEREOF

This invention relates to a method of controlling ectoparasitic species of *Acarina* on warm-blooded animals which comprises orally administering to said animals an ectoparasitically effective amount of an 2-aryl-1,3-cyclohexandione compound and their alkali metal salts, ammonium salts and enol ester derivatives.

More particularly, this invention relates to a method of controlling ectoparasitic species of *Acarina* on warmblooded animals which comprises orally administering to said animals an ectoparasitically effective amount of a compound of the formula:

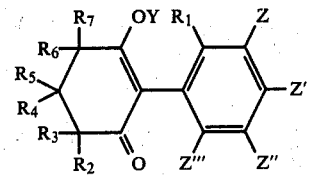

and alkali metal salts and ammonium salts thereof wherein:

Z, Z', Z" and Z''' are individually hydrogen, haloalkyl, polyhaloalkyl, halogen, alkyl, alkoxy, cyano, nitro, alkylthio, alkylsulfinyl, alkylsulfonyl, alkanoyl, amido or amino;
Y is hydrogen or

R is hydrogen, halogen, alkyl, alkenyl, alkynyl, bicycloalkyl, bicycloalkenyl, cycloalkyl, cycloalkenyl, haloalkyl, phenyl, phenylalkyl, naphthyl or naphthylalkyl, all of which, other than hydrogen and halogen, may be substituted with one or more alkyl, cyano, nitro, alkoxy, halogen, haloalkyl, alkylthio, alkylsulfinyl, alkylsulfonyl, alkoxyalkyl, alkylthioalkyl, alkylsulfinylalkyl, alkylsulfonylalkyl or dialkylamino substituents.
$R_1$ is alkyl, polyhaloalkyl or haloalkyl or halogen;
$R_2$, $R_3$, $R_4$, $R_5$, $R_6$ and $R_7$ are individually hydrogen or either substituted or unsubstituted alkyl or phenyl, wherein the permissible substituents are one or more alkyl, cyano, halogen, nitro, alkoxy, alkylthio, alkylsulfinyl, alkylsulfonyl or dialkylamino substituents; or any two $R_2$, $R_3$, $R_4$, $R_5$, $R_6$ or $R_7$ substituents together may form an alkylene or alkenylene chain having from 2 to 20 carbon atoms completing a 3, 4, 5, 6 or 7 membered ring structure;
with the proviso that $R_1$, $R_2$, $R_3$, $R_4$, $R_5$, $R_6$, $R_7$, Z, Z', Z", and Z''' individually may not include more than ten aliphatic carbon atoms and R may not include more than thirty aliphatic carbon atoms.

The following ectoparasitically active compounds are illustrative of compounds within the purview of the above generic formula that can be utilized in the claimed process and which can be conveniently prepared by the process hereinbelow simply by selecting appropriate reactants for use in the procedures described below:

2-(2'-Chlorophenyl)-3-(7-phenylheptanoyloxy)-5,5-dimethyl-2-cyclohexenone.

2-(2'-Chlorophenyl)-3-(2',6'-dichlorohexanoyloxy)-2-cyclohexenone 2-(2'-4'-Dibromophenyl)-3-(hexanoyloxy)-2-cyclohexenone 2-(2'-Chlorophenyl)-3-(2-ethylhexanoyloxy)-2-cyclohexenone 3-(2'-Isopropylphenyl)-4-acetoxy-spiro[5.5]undec-3-en-2-one 2-(2'-Chlorophenyl)-3-benzoyloxy-5,5-dimethyl-2-cyclohexenone 2-(2'-Bromophenyl)-3-(4'-chlorobenzoyloxy)-5,5-dimethyl-2-cyclohexenone 2-(2'-Chlorophenyl)-3-(5'-diethylaminophenylcarbonyloxy)-5,5-dimethyl-2-cyclohexenone 2-(2'-Chlorophenyl)-3-(4'-chlorophenylcarbonyloxy)5,5-dimethyl-2-cyclohexenone 2-(2'-Chlorophenyl)-3-(4'-methylthiophenylcarbonyloxy)-5,5-dimethyl-2-cyclohexenone 2-(2'-chloro-5'-Nitrophenyl)-3-(4'-dimethylaminophenylcarbonyloxy)-5,5-dimethyl-2-cyclohexenone 2-(2'-Chlorophenyl)-3-(trifluoroacetoxy)-5,5-dimethyl-2-cyclohexenone 2-(2'-Chlorophenyl)-3-(acetoxy)-5,5-dimethyl-2-cyclohexenone.

2-(2'-Trifluoromethyl-4'-nitrophenyl)-3-chlorocarbonyloxy-5,6-dimethyl-2-cyclohexenone 2-(2'-Methyl-4'-nitrophenyl)-3-chlorocarbonyloxy-5,6-dimethyl-2-cyclohexenone 2-(2'-Methyl-6'-nitrophenyl)-3-naphthylcarbonyloxy-4,4-diethyl-2-cyclohexenone 2-(2'-4'-Dimethylphenyl)-3-hexanoyloxy-5,5-dimethyl-2-cyclohexenone 2-(2',4'-Dimethylphenyl)-3-(2-ethylhexanoyloxy)-5,5-dimethyl-2-cyclohexenone 2-(2',3'-Dimethylphenyl)-3-stearoyloxy-5,5-dimethyl-2 cyclohexenone 2-(2',5'-Dichlorophenyl)-3-acetoxy-5,5-dimethyl-2-cyclohexenone 2-(2',4'-Dibromophenyl)-3-isobutyrloxy-5,5-dimethyl-2-cyclohexenone 2-(2',6'-Dichlorophenyl)-3-hexanoyloxy-5,5-dimethyl-2-cyclohexenone 2-(2',6'-Dichlorophenyl)-3-(2-ethylhexanoyloxy)-5,6-dimethyl-2-cyclohexenone 2-(2',5'-Dichlorophenyl)-3-stearoyloxy-5,5-dimethyl-2-cyclohexenone 2-(2',3'-Dimethylphenyl)-3-benzoyloxy-5,5-dimethyl-2-cyclohexenone 2-(2',4'-Dimethylphenyl)-3-phenylcarbonyloxy-4,6-dimethyl-2-cyclohexenone 2-(2',4'-Difluorophenyl)-3-(2',4'-dichlorophenylcarbonyloxy)-5,5-dimethyl-2-cyclohexenone 2-(2',4'-Dimethylphenyl)-3-(4'-dimethylaminophenylcarbonyloxy-5,5-dimethyl-2-cyclohexenone 2-(2',4'-Dimethylphenyl)-3-(4'-chlorophenylcarbonyloxy)-5,6-dimethyl-2-cyclohexenone 2-(2',4'-Dimethylphenyl)-3-(2'-ethylthiophenylcarbonyloxy)-5,5-dimethyl-2-cyclohexenone 2-(2',4'-Dimethylphenyl)-3-trifluoroacetoxy-5,5-dimethyl-2-cyclohexenone 2-(2',4'-Dimethylphenyl)-3-dimethylaminoacetoxy-4,5-dimethyl-2-cyclohexenone 2-(2',4'-Dimethylphenyl)-3-methylthioacetoxy-5,5-dimethyl-2-cyclohexenone 2-(2',4'-Dimethylphenyl)-3-methylsulfonylacetoxy-5,5-dimethyl-2-cyclohexenone 2-(2',4'-Dimethylphenyl)-3-(2-cyclohexenylcarbonyloxy)-5,5-dimethyl-2-cyclohexenone 2-(2'-Trichloromethyl-4'-nitrophenyl)-3-(2',4-dicyanohexanoyloxy)-4-(2'-chloroethyl)-2-cyclohexenone 2-(2'-Chloro-4'-nitrophenyl)-3-(2'-nitroethanoyloxy)-4,5-diethyl-2-cyclohexenone 2-(2'-Chloro-6'-methoxy-4'-nitrophenyl)-3-pentanoyloxy-6-(2'-cyanoethyl)-2-cyclohexenone 2-(2'-Chlorophenyl)-3-acetoxy-5,5-dimethyl-2-cyclohexenone 2-(2'-Chlorophenyl)-3-(cyclopropylcarbonyloxy)-4,5-dimethyl-2-cyclohexenone 2-(2'-Bromophenyl)-3-(2-ethylhexanoyloxy)-5,6-dimethyl-2-cyclohexenone 2-(2',4',6'-Trimethylphenyl)-3-(4'-cyanobenzoyloxy)-4-methyl-2-cyclohexenone 2-(2'-Methylphenyl)-3-ethanoyloxy-5-(3'-ethylsulfinylphenyl)-2-cyclohexenone 2-(2'-Methylphenyl)-3-(4'-methoxyphenylcarbonyloxy)-5,5-dimethyl-2-cyclohexenone 2-(2',6'-Dimethylphenyl)-3-(2',4'-dicyanophenylcarbonyloxy)-5,5-dimethyl-2-cyclohexenone 2-(2',4'-Dimethylphenyl)-3-(3'-nitrophenylcarbonyloxy)-5,5-dimethyl-2-cyclohexenone 2-(2'-Methyl-4'-chlorophenyl)-3-(trifluoroacetoxy)-5,5-dimethyl-2-cyclohexenone 2-(2',4'-Dimethylphenyl)-3-(3'-methylthiobenzoyloxy)-5,5-dimethyl-2-cyclohexenone 2-(2'-Methylphenyl)-3-(2'-methylsulfinylbenzoyloxy)-5,5-dimethyl-2-cyclohexenone 2-(2'-Methylphenyl)-3-(4'-methylsulfonylphenylcarbonyloxy)-5,5-dimethyl-2-cyclohexenone 2-(2',4',6'-Trimethylphenyl)-3-cyclopropylcarbonyloxy-5,5-dimethyl-2-cyclohexenone 2-(2',4',6'-Trimethylphenyl)-3-(2-cyclohexenylcarbonyloxy)-5,5-dimethyl-2-cyclohexenone 2-(2'-Methylphenyl)-3-propynoyloxy-5,5-dimethyl-2-cyclohexenone 4-Acetoxy-3-(2',4'-dimethylphenyl)-bicyclo[3.2.1]oct-3-en-2-one 4-(2-Ethylhexanoyloxy)-3-(2'-chlorophenyl)-spiro[5.5]undec-3-en-2-one 2-Hexanoyloxy-3-(2',4'-dichlorophenyl)-bicyclo[4.4.0]dec-2-en-4-one 3-Isobutyryloxy-4-(4'-chlorophenyl)-2-(2',5'-dimethylphenyl)-2-cyclohexenone 2-(2',4',6'-Trimethylphenyl)-1,3-cyclohexanedione 2-(2'-Cyano-4',6'-dichlorophenyl)-1,3-cyclohexanedione 2-(2'-Isopropyl-6'-cyanophenyl)-4,6-dimethyl-1,3-cyclohexanedione 2-(2'-Trifluoromethyl-6'-methyl)-4-trichloromethyl-1,3-cyclohexanedione Triethylammonium salt of 2-(2',4'-dimethylphenyl)-5,5-dimethyl-1,3-cyclohexanedione Pyrrolidinium salt of 2-(2',4'-dichlorophenyl)-5,5-dimethyl-1,3-cyclohexanedione Piperidinium salt of 2-(2',5'-dimethylphenyl)-5,5-dimethyl-1,3-cyclohexanedione 1-Adamantanammonium salt of 2-(2'-chlorophenyl)-5,5-dimethyl-1,3-cyclohexanedione Pyridinium salt of 2-(2'-methylphenyl)-5,5-dimethyl-1,3-cyclohexanedione Morpholinium salt of 2-(2',4'-dichlorophenyl)-5,5-dimethyl-1,3-cyclohexanedione Benzyldimethylammonium salt of 2-(2',4'-dimethylphenyl)-5,5-dimethyl-1,3-cyclohexanedione Dicyclohexylammonium salt of 2-(2'-chlorophenyl)-5,5-dimethyl-1,3-cyclohexanedione N,N-diethylanilinium salt of 2-(2',4'-dimethylphenyl)-5,5-dimethyl-1,3-cyclohexanedione 2-Picolinium salt of 2-(2',4'-dichlorophenyl)-5,5-dimethyl-1,3-cyclohexanedione Piperazinium salt of 2-(2',5'-dimethylphenyl)-5,5-dimethyl-1,3-cyclohexanedione Imidazolinium salt of 2-(2'-chlorophenyl)-5,5-dimethyl-1,3-cyclohexanedione 2-(2',4'-dimethylphenyl)-5-methyl-5-ethyl-1,3-cyclohexanedione 2-(2',4'-dichlorophenyl)-5,5-diethyl-1,3-cyclohexanedione 2-(2'-methyl-4'-methoxyphenyl)-5-methyl-5-isobutyl-1,3-cyclohexanedione 2-(2'-methyl-4'-chlorophenyl)-5-methyl-5-isopropyl-1,3-cyclohexanedione 2-(2'-Ethyl-6'-ethoxyphenyl)-5,5-dimethyl-1,3-cyclohexanedione 2-(2',6'-Diethylphenyl)-5,5-ditrifluoromethyl-1,3-cyclohexanedione 2-(2'-Methyl-6'-(methylsulfinyl)phenyl)-5,5-dimethyl-1,3-cyclohexanedione 2-(2'-Trichloromethyl-6'-cyanophenyl)-5,6-dimethyl-1,3-cyclohexanedione 2-(2',6'-Dimethyl-4'-t-butylphenyl)-5,5-dimethyl-1,3-cyclohexanedione 3-(2',4',6'-Triethylphenyl)-spiro-[5,5]undecane-2,4-dione Trimethylammonium salt of 2-(2'-ethyl-6'-ethoxy)-5,5-dimethyl-1,3-cyclohexanedione 3-(2'-Methylphenyl)-spiro[5.5]undecane-2,4-dione 5-Phenyl-2-(2',4',6'-trimethylphenyl)-1,3-cyclohexanedione 2-(2'-Methyl-4',6'-dichlorophenyl)-5,5-dimethyl-1,3-cyclohexanedione 2-(2'-Nitro-4',6'-Dibromophenyl)-5,5-dimethyl-1,3-cyclohexanedione 5-(4'-Chlorophenyl)-2-(2',4',6'-trimethylphenyl)-1,3-cyclohexanedione 5-(3'-Bromophenyl)-2-(2',4',6'-trimethylphenyl)-1,3-cyclohexanedione 5-(2'-Methylthiophenyl)-2-(2',4',6'-trichlorophenyl)-1,3-cyclohexanedione 5-(4'-Methoxyphenyl)-2-(2',4',6'-trimethylphenyl)-1,3-cyclohexanedione 5-(3'-β-methoxyethylphenyl)-2-(2',4',6'-trimethylphenyl)-1,3-cyclohexanedione 2-(2',4',6'-Trimethylphenyl)-4-(4'-methylphenyl)-5,5-dimethyl-1,3-cyclohexanedione 2-(2',4',6'-Trimethylphenyl)-4-phenyl-5,5-dimethyl-1,3-cyclohexanedione 2-(2',4',6'-Trimethylphenyl)-4-(4'-chlorophenyl)-5,5-dimethyl-1,3-cyclohexanedione 2-(2',4',6'-Trimethylphenyl)-4-methoxy-5,5-dimethyl-1,3-cyclohexanedione 2-(2',4',6'-Trimethylphenyl)-4,5-dimethyl-1,3-cyclohexanedione 2-(2',4',6'-Trimethylphenyl)-4-(4'-dimethylaminophenyl)-5-methyl-1,3-cyclohexanedione 5-(4'-Dimethylaminophenyl)-2-(2',6'-dimethylphenyl)-4-methyl-1,3-cyclohexanedione 2-(2'-N-methylcarbamoyl-6'-methylphenyl)-4-(4'-methoxyphenyl)-5,6-dimethyl-1,3-cyclohexanedione 2-(2',6'-Dimethylphenyl)-4-(4'-methylthiophenyl)-5,5-dimethyl-1,3-cyclohexanedione 2-(2'-Methyl-3',6'-dicyanophenyl)-6-(methylthioethyl)-1,3-cyclohexanedione 5-(4'-Methylsulfinylphenyl)-4,6-dimethyl-2-(2',6'-Dimethylphenyl)-1,3-cyclohexanedione N-Methylpiperdinium salt of 5-(2'-Methoxyphenyl)-2-(2',4',6'-trimethylphenyl)-1,3-cyclohexanedione Trimethylammonium salt of 2-(2',6'-Dimethylphenyl)-4-(4'-methylthiophenyl)-5,6-dimethyl-1,3-cyclohexanedione 2-(2'-Chloro-4'-methoxyphenyl)-5,5-dimethyl,-1,3-cyclohexanedione 2-(2'-Methyl-4'-cyanophenyl)-5,5-dimethyl-1,3-cyclohexanedione 2-(2'-Methyl-4'-trifluoromethylphenyl)-5,5-dimethyl-1,3-cyclohexanedione 2-(2'-Trifluoromethyl-4'-methoxyphenyl)-5,5-dimethyl-1,3-cyclohexanedione 2-(2'-Trifluoromethyl-4'-chlorophenyl)-5,5-dimethyl-1,3-cyclohexanedione 2-(2'-Trifluoromethyl-4'-cyanophenyl)-5,5-dimethyl-1,3-cyclohexanedione 2-(2',4'-Dimethylphenyl)-5-phenyl-1,3-cyclohexanedione 2-(2'-Methylphenyl)-5-(2'-methylsulfonylmethyl)-1,3-cyclohexanedione 2-(2'-Methylphenyl)-5-(2'-chlorophenyl)-1,3-cyclohexanedione 2-(2'-Methylphenyl)-5-(4'-nitrophenyl)-1,3cyclohexanedione 2-(2'-Methylphenyl)-5-(4'-cyanophenyl)-1,3-cyclohexanedione 2-(2',4'-Dimethylphenyl)-5-(2'-methylphenyl)-1,3-cyclohexanedione 2-(2',4'-Dimethylphenyl)-4-(4'-trifluoromethylphenyl)-1,3-cyclohexanedione 2-(2',4'-Dimethylphenyl)-5-(2'-chlorophenyl)-1,3-cyclohexanedione 2-(2',4'-Dichlorophenyl)-6-(2'-methylthiophenyl)-1,3-cyclohexanedione 2-(2',4'-Dichlorophenyl)-5-(4'-methylphenyl)-1,3-cyclohexanedione 2-(2',4'-Dichlorophenyl)-5-(4'-methoxyphenyl)-1,3-cyclohexanedione 3-(2'-Methylphenyl)-spiro[5.5]undecane-2,4-dione 3-(2',4'-Dimethylphenyl)-spiro[5.5]undecane-2,4-dione 3-(2'-Chlorophenyl)-spiro[5.5]undecane-2,4-dione 3-(2',4'-Dichlorophenyl)-spiro[5.5]undecane-2,4-dione 2-(2',4'-Dimethylphenyl)-4,5-diethyl-1,3-cyclohexanedione 2-(2',4'-Difluorophenyl)-6-methyl-1,3-cyclohexanedione 2-(2'-methyl-5'-cyanophenyl)-6-methoxymethyl-1,3-cyclohexanedione 2-(2',4'-Dibromophenyl)-4-(4'-methylthiophenyl)-5-methyl-1,3-cyclohexanedione 2-(2',4'-Dichlorophenyl)-6-(4'-dimethylaminophenyl)-1,3-cyclohexanedione 2-(2'-Trifluoromethyl-5-cyanophenyl)-6-methylsulfinylethyl-1,3-cyclohexanedione 2-(2'-chloro-4'-methoxyphenyl)-4,6-dimethyl-1,3-cyclohexanedione The pyridinium salt of 2-(2',4'-Dibromophenyl)-6-methoxymethyl-1,3-cyclohexanedione The N-methylmorpholinium salt of 2-(2'-methylphenyl)-4,6-diethyl-1,3-cyclohexanedione 5-(2',4'-Dimethylphenyl)-2-(2',4',6'-trichlorophenyl)-1,3-cyclohexanedione 5-(2',4'-Dichlorobutyl)-2-(2'-ethoxy-3',5',6'-trifluorophenyl)-1,3-cyclohexanedione 5-(Methylthiomethyl)-2-(2'-chloro-6'-cyanophenyl)-1,3-cyclohexanedione 5-(2'-Dimethylaminophenyl)-2-(2',6'-dimethylphenyl)-1,3-cyclohexanedione 2-(2'-Nitro-3'-methylthio-6'-trichloromethylphenyl)-5,5-dimethyl-1,3-cyclohexanedione 2-(2'-methyl-5'-cyano-6'-nitrophenyl)-4,6-dimethyl-1,3-cyclohexanedione 2-(2',4'-Dichloro-6'-trifluoromethylphenyl)-4-(2'-chloroethyl)-1,3-cyclohexanedione 3-(2'-Chloro-6'-fluorophenyl)-spiro[5.5]-undecane-2,4-dione 2-(2'-Chloro-4'-nitro-6'-cyanophenyl)-5,5-propyl-1,3-cyclohexanedione 2-(2',6'-Dichloro-4'-nitrophenyl)-5-(2'-cyanoethyl)-1,3-cyclohexanedione 2-(2'-Chloro-6'-methoxy-4'-nitrophenyl)-5,5-dimethyl-1,3-cyclohexanedione 2-(2'-Chloro-6'-cyano-4'-nitrophenyl)-5,5-dimethyl-1,3-cyclohexanedione 2-(2'-Bromo-6'-methoxyphenyl)-1,3,-cyclohexanedione 2-(2'-Methyl-6'-nitrophenyl)-1,3,-cyclohexanedione 2-(2'-Trifluoromethyl-6'-nitrophenyl)-1,3-cyclohexanedione 2-(2',6'-Dichloro-4'-nitrophenyl)-1,3-cyclohexanedione 2-(2'-Chloro-6'-methoxy-4'-nitrophenyl)-1,3-cyclohexanedione 2-(2'-Chloro-6'-cyano-4'-nitrophenyl)-1,3-cyclohexanedione 2-(2'-Chloro-4',6'-dinitrophenyl)-1,3-cyclohexanedione 2-(2'-Methyl-4',6'-dinitrophenyl)-1,3-cyclohexanedione 4-(4'-Chlorophenyl)-2,(2'-chloro-4'-nitrophenyl)-1,3-cyclohexanedione 5-(4'-Cyanophenyl)-2-(2'-chloro-6'-methoxy-4'-nitrophenyl)-1,3-cyclohexanedione 5-(2',4'-Dichlorophenyl)-2-(2',4'-dichloro-6'-nitrophenyl)-1,3-cyclohexanedione 5-(3'-Nitrophenyl)-2-(2'-chloro-4'-nitrophenyl)-1,3-cyclohexanedione 5-Phenyl-2-(2'-methyl-6'-chloro-4'-nitrophenyl)-1,3-cyclohexanedione 3-(2'-Chloro-6'-nitrophenyl)-spiro[5.5]undecane-2,4-dione 3-(2',6'-Dichloro-4'-nitrophenyl)-spiro[5.5]undecane-2,4-dione 2-(2'-Trifluoromethyl-4'-aminophenyl)-5,5-dimethyl-1,3-cyclohexanedione 2-(2',4'-Dichloro-6'-aminophenyl)-5,5-dimethyl-1,3-cyclohexanedione 2-(2',6'-Dichloro-4'-aminophenyl)-5,6-dimethyl-1,3-cyclohexanedione 2-(2'-Chloro-6'-nitro-4'-aminophenyl)-5,5-dimethyl-1,3-cyclohexanedione 5-(4'-Chlorophenyl)-2-(2'-chloro-6'-methoxy-4'-aminophenyl)-1,3-cyclohexanedione
5-(4'-Chloro-6'-nitrophenyl)-2-(2'-bromo-4'-methylsulfinyl-6'-cyanophenyl)-1,3-cyclohexanedione
3-(2'-Chloro-6'-aminophenyl)-spiro[5.5]undecane-2,4-dione
2-(2',6'-Dichloro-4'-aminophenyl)-1,3-cyclohexanedione
2-(2'-Methyl-6'-nitrophenyl)-5-methoxymethyl-1,3-cyclohexanedione
2-(2'-Chloro-6'-nitrophenyl)-5,5-dimethyl-1,3-cyclohexanedione
2-(2'-Methyl-6'-nitrophenyl)-1,3-cyclohexanedione
2-(2'-Chloro-6'-nitrophenyl)-1,3-cyclohexanedione
2-(2'-Chloro-6'-methoxyphenyl)-5,6-dimethyl-1,3-cyclohexanedione
2-(2'-Chloro-6'-methoxyphenyl)-4,4-dimethyl-1,3-cyclohexanedione
2-(2'-Methyl-3'-nitro-6'-methoxyphenyl)-4,5-dimethyl-1,3-cyclohexanedione
2-(2'-Chloro-6'-methoxyphenyl)-1,3-cyclohexanedione
2-(2'-Methyl-4'-nitro-6'-methoxyphenyl)-1,3-cyclohexanedione
2-(2'-Bromo-4'-nitro-6'-idophenyl)-4,5-dimethyl-1,3-cyclohexanedione
2-(2'-Bromo-4'-aminophenyl)-5,5-dimethyl-1,3-cyclohexanedione
2-(2',6'-Dibromophenyl)-5,5-dimethyl-1,3-cyclohexanedione
2-(2'-Bromo-6'-aminophenyl)-1,3-cyclohexanedione
2-(2'-Bromo-5'-chloro-6'-fluorophenyl)-1,3-cyclohexanedione
2-(2',4'-Dichlorophenyl)-5,5-dimethyl-1,3-cyclohexanedione
2-(2'4'-Dichloro-6'-tribromomethylphenyl)-1,3-cyclohexanedione
2-(2',4',6'-Trifluorophenyl)-5,5-dimethyl-1,3-cyclohexanedione
2-(2',4',6'-Tribromophenyl)-1,3-cyclohexanedione
3-(2'-Chloro-6'-bromophenyl)-spiro[5.5]undecane-2,4-dione
3-(2',4',6'-Trimethylphenyl)-spiro[5.5]undecane-2,4-dione
3-(2',4',6'-Trichlorophenyl)-spiro[5.5]undecane-2,4-dione
2-(2'-Methyl-6'-cyano-5'-nitrophenyl)-5,5-dimethyl-1,3-cyclohexanedione
2-(2'-Methyl-6'-cyano-4'-nitrophenyl)-1,3-cyclohexanedione
2-(2'-Chloro-6'-cyanophenyl)-1,3-cyclohexanedione
2-(2'-Chloro-4'-cyanophenyl)-6-trichloromethyl-1,3-cyclohexanedione
2-(2',6'-Dichloro-4'-cyanophenyl)-1,3-cyclohexanedione
5-(2',4'-Dimethoxyphenyl)-2-(2',6'-dimethylphenyl)-1,3-cyclohexanedione
5-(2'-Cyanopropyl)-6-methyl-2-(2',6'-dimethylphenyl)-1,3-cyclohexanedione
5-(3'-Ethylsulfinylphenyl)-2-(2',6'-dichlorophenyl)-1,3-cyclohexanedione
3-(2',4'-Dimethylphenyl)-bicyclo[3.2.1]octane-2,4-dione
3-(2',4'-Dichlorophenyl)-bicyclo[4.4.0]decane-2,4-dione All compounds within the purview of the above generic formula exhibit ectoparasiticidal activity to a lesser or greater extent when orally administered to warm-blooded animals. Some of these compounds exhibit very high levels of ectoparasiticida in extremely small dosages while others require larger dosages to be ectoparasiticidally effective. These compounds are relatively non-toxic to warm-blooded animals when used in an amount sufficiently to contro Dcarma ectoparasites. Ectoparasiticidal activity is greatest in those compounds having a hydrogen, alkyl, alkoxy, cyano, trihalomethyl or halogen substituent at one of the ortho positions of the 2-phenyl moiety and an alkyl or halogen substituent at the other ortho position of the 2-phenyl moiety. Especially active compounds are those in which the ortho substituents are relatively small groups such as methoxy, ethoxy, methyl, ethyl, or halogen.

Preferred for use in the method of this invention because of their higher levels of ectoparasiticidal activity are the compounds in which, Y is hydrogen or

Z, Z', Z" and Z'" are individually hydrogen, alkyl, alkoxy, cyano, halogen, or trihalomethyl;

$R_1$ is alkyl or halogen;

$R_2$, $R_3$, $R_4$, $R_5$, $R_6$ and $R_7$ are individually hydrogen or alkyl;

The most active and particularly preferred for use in the method of this invention are compounds in which:

Z, Z', Z" and Z'" are individually hydrogen, methyl, methoxy, cyano or halogen;

R is a linear or branched chain alkyl moiety having from 1 to 30 carbon atoms or hydrogen;

$R_1$ is methyl or halogen;

$R_2$, $R_3$, $R_4$, $R_5$, $R_6$ and $R_7$ are individually hydrogen, methyl or ethyl.

The 2-aryl-1,3-cyclohexanedione enol ester compounds used in the method of this invention can be conveniently prepared by a variety of methods. Two preferred methods which utilize the 2-aryl-1,3-cyclohexanedione parent compound as the precursor are illustrated by the general reaction schemes set forth below in which R, $R_1$, $R_2$, $R_3$, $R_4$, $R_5$, $R_6$, $R_7$, Z, Z', Z" and Z'" are as described above and X is hydrogen, hydroxyl or

except as noted:

METHOD I

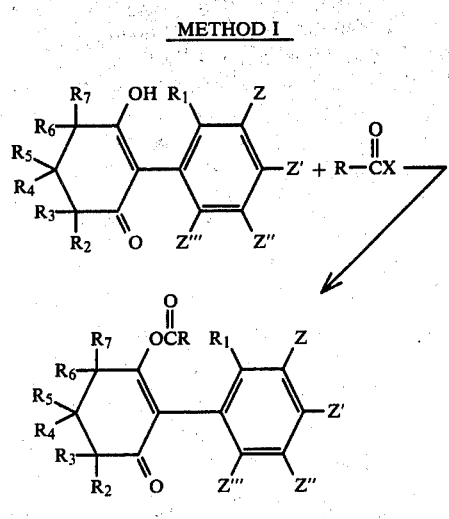

In the reaction illustrated in METHOD I, one equivalent of the corresponding 2-arylcyclohexane-1,3-dione compound is reacted with an appropriately substituted acid, acid halide or anhydride compound in the presence of at least one equivalent of an acid acceptor, preferably in an inert solvent.

The acid acceptor utilized in the reactions of METHOD I can be either an organic or an inorganic base. Illustrative of organic bases that are useful as acid acceptors in the conduct of these reactions one can mention, aromatic or heterocyclic tertiary amine compounds such as pyridine or N,N-dimethylaniline, linear tertiary amines, such as triethylamine, pyridine, trimethylamine or 1,4-diazobicyclo[2.2.2] octane; or alkali metal alkoxides, as for example, sodium methoxide, sodium ethoxide or the like. Bases such as sodium carbonate, sodium hydroxide or potassium hydroxide are illustrative of inorganic bases that are useful as acid acceptors. Preferred organic acid acceptors are tertiary amines such as triethylamine, pyridine or trimethylamine.

In general, any organic solvent that is inert to the reactants or reaction conditions may be employed in the reaction of METHOD I. Illustrative of organic solvents which are generally suitable for use in the conduct of these reactions are saturated, unsaturated and aromatic hydrocarbons, e.g. hexane, cyclohexane, octane, cyclohexene, dodecane, naphtha, decalin, kerosene, cycloheptane, benzene, toluene, xylene, naphthalene or the like; ethers such as dioxane, tetrahydrofuran, diethyl ether, tetrahydropyran, 1,2-dimethoxybenzene, 1,2-diethyl benzene, the dialkyl ethers of ethylene glycol, of propylene glycol or chlorinated aliphatic hydrocarbons as for example, chloroform, dichloromethane, methylene dichloride, 1,1-dichloroethane, carbon tetrachloride or the like.

The 2-aryl-1,3-cyclohexanedione compounds of this invention can be conveniently prepared by a variety of methods. Two preferred methods for preparing the compounds of this invention are illustrated by the reaction schemes set below in which $R_1$, $R_2$, $R_3$, $R_4$, $R_5$, $R_6$, $R_7$, $Z$, $Z'$, $Z''$ and $Z'''$ are as described above and $R_8$ is alkyl except as noted:

METHOD II

METHOD III

Preferably, the reactions illustrated in METHODS I and II are carried out by contacting equivalent amounts of the reactants in a suitable solvent. In the conduct of the reaction of METHOD II, types and quantities of the solvent employed are not critical. Illustrative of suitable inert solvents are ethanol, methanol, dimethylformamide, dimethylsulfoxide, methylene chloride, benzene, xylene, toluene, dioxane, dimethoxyethane, tetrahydrofuran and the like.

The reaction illustrated in METHOD I can be conducted in any solvent that is chemically inert to the reactants and to the reaction conditions, and in which the acid catalyst is soluble. Illustrative of such solvents are water and carboxylic acids, such as acetic acid, butanoic acid, or the like. The preferred reaction solvents are water and acetic acid.

The cyclization reaction illustrated in METHOD I is conducted in the presence of a strong mineral acid catalyst. Illustrative of mineral acids that are useful in the conduct of this reaction are sulfuric acid, hydrochloric acid, perchloric acid and the like. The preferred acid catalyst is sulfuric acid.

The quantity of acid catalyst employed in the conduct of the reaction of METHOD II is not critical. In general, to achieve a reasonable rate of reaction, the reaction is conducted in the presence of from about 1 to about 85 weight percent of the acid catalyst based on the total weight of the reaction solvent. Preferred acid concentrations are from about 50 to about 85 weight percent based on the weight of the reaction solvent.

The cyclization reaction illustrated in METHOD III is conducted in the presence of at least one equivalent of either a strong organic or a strong inorganic base. Illustrative of bases that are useful in the conduct of this reaction are the alkali metal alkoxides, as for example, sodium methoxide, sodium ethoxide or potassium tert-butoxide; the alkali metal alkylides; or the alkali metal hydrides such as sodium hydride, lithium hydride or the like. The preferred base in the conduct of this reaction is sodium hydride.

Alternative procedures for preparing a more limited class of 2-aryl-1, 3-cyclohexanedione compounds are illustrated by the general reaction schemes set forth below in which $R_1$, $R_2$, $R_3$, $R_4$, $R_5$, $R_6$, $R_7$, Z, Z', Z'' and Z''' are as described above and X is fluorine or chlorine except as noted:

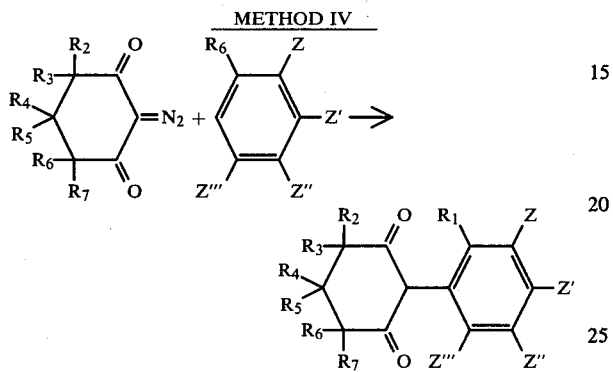

In METHOD IV, $R_1$ is alkyl and Z, Z', Z'' and Z''' are other than nitro.

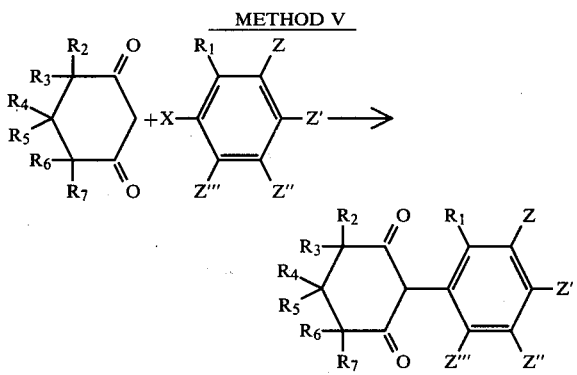

In Method V, Z' is alkylsulfonyl or nitro; or Z' may also be alkyl or alkoxy when either $R_1$ or Z''' is nitro.

The procedure illustrated in METHOD IV involves the photosensitized decomposition of a 2-diazocycloalkane-1, 3-dione compound in an aromatic solvent, in the presence of a photosensitizer, preferably benzophenone. In this procedure an appropriately substituted 2-diazocycloalkane-1, 3-dione compound is photochemically decomposed to form the corresponding triplet carbene which, in turn, reacts with a suitable aromatic solvent to form the desired 2-arylcycloalkane-1, 3-dione compound. The photolysis reaction is carried out using ultraviolet radiaton having a wavelength of greater than 290 nanometers. The ultraviolet radiation can be obtained from any conventional ultraviolet radiation source known to those skilled in the photolysis art. Illustrative of suitable sources for generating ultraviolet radiation are high and low pressure mercury arc lamps, germacidal lamps, "black" lights and the like.

Preferably the reaction illustrated in METHOD V is carried out by contacting equivalent amounts of the reactants in an appropriate solvent, in the presence of at least an equivalent of either an organic or an inorganic base. Illustrative of suitable reaction solvents, are dimethylformamide, dimethylsulfoxide, hexamethylphosphoramide and the like. Illustrative of bases that may be utilized in the conduct of this reaction are alkali metal carbonates or bicarbonates, as for example, sodium bicarbonate or potassium carbonate; alkali metal hydrides, such as lithium hydride, sodium hydride or potassium hydride, or alkali metal alkoxides or hydroxides, such as sodium hydroxide, sodium methoxide or potassium tert-butoxide. The preferred base is anhydrous potassium carbonate.

The reactions of METHODS I to V are neither temperature nor pressure sensitive and may be conducted over a broad temperature and pressure range to yield the desired product. In general, these reactions can be conducted at a temperature of from about −30° C. to about 200° C. For convenience these reactions are conducted at autogeneous or atmospheric pressure.

The alkali metal and ammonium salts of the compounds of this invention can be conveniently prepared in accordance with conventional methods. For example, the alkali metal and ammonium salts can be prepared by treating the corresponding 2-aryl-1, 3-cyclohexanedione compound with an alkali metal alkoxide, or ammonia, or an amine respectively.

The 6-aryl-5-ketopolyalkylhexanoic acid compounds utilized as reactants in the reaction illustrated in METHOD I can be conveniently prepared by reacting an appropriately polysubstituted benzyl cyanide compound with a suitable polyalkyl glutaric acid derivative in the presence of base to form the corresponding 6-aryl-6-cyano-5-ketopolyalkylhexanoic acid ester compound which, in turn, is hydrolyzed under acidic conditions to the desired reactant.

The 6-aryl-5-ketopolyalkylhexanoic acid ester compounds utilized as reactants in the reaction illustrated in METHOD II can be conveniently prepared by esterifying the 6-aryl-5-ketopolyalkylhexanoic acid reactant of METHOD I via conventional esterification techniques.

The 2-diazo-1, 3-cyclohexanedione compounds utilized as reactants in the reaction of Method III can be prepared by treating an appropriately substituted cyclohexanedione-1, 3-dione compound with a sulfonyl azide in the presence of an acid acceptor, as for example, a trialkylamine, as described in more detail in H. Stetter and K. Kiehr, Chem. Ber., 98 1181 (1965), M. Regitz and P. Stodler, Liebigs Ann. Chem., 687, 214 (1967) and references cited therein. The cyclohexane-1, 3-dione compound, in turn, can be prepared by conventional methods, as for example by condensing an appropriately substituted αβ-unsaturated ketone with diethyl malonate in the presence of a base catalyst as described in more detail in K. W. Rosenmund, H. Herzberg and H. Scutt, Chem. Ber., 87, 1258 (1954), C. K. Shuang and Y. L. Tien, Chem. Ber., 69, 27 (1936) and references cited therein.

The substituted aryl, cyclohexanedione, acid halide, acid and anhydride compounds employed as reactants in the reactions illustrated in METHOD I and V are known classes of compounds that can be either obtained from commercial sources or prepared in accordance with conventional methods known to those skilled in the synthetic arts.

The following specific examples are present to more particularly illustrate the preparation of the compounds utilized in the method of this invention.

EXAMPLE I

Preparation of
2-(2'-Chloro-4'-Nitrophenyl)-5,5-dimethyl-1,3-cyclohexanedione

A solution containing 42.05 g (0.300 mol) of 5,5-dimethyl-1,3-cyclohexanedione and 100 g (0.718 g-atom) of anhydrous potassium carbonate in 300 ml of dry dimethylformamide was heated to 75° C. under nitrogen and stirred for one hour. The 3,4-dichloronitrobenzene, 57.60 g (0.300 mol) was dissolved in 100 ml dimethylformamide and added dropwise to the reaction mixture while stirring and maintaining the temperature of the reaction mixture at 75° C. A deep red-colored solution formed, and when the addition was complete the reaction temperature was raised to 100° C. and held at this temperature for 3 hours. Most of the dimethylformamide was removed by vacuum distillation. The residue was poured into 2 l of ice water and extracted three times with 500 ml of benzene. Nitrogen was then passed through the aqueous solution while warming to remove dissolved benzene. The aqueous solution was cooled in an ice bath and acidified to give a tacky precipitate, which, upon warming solidified and was collected by suction filtration. The product was recrystallized from acetone to give 31.7 g (36%) of 2-(2'-Chloro-4'-nitrophenyl)-5,5-dimethyl-1, 3-cyclohexanedione as a white powder, m.p. 250°–253° C.

Calculated for $C_{14}H_{14}ClNO_4.\frac{1}{2}H_2O$: C, 55.18; H, 4.96; N, 4.60. Found: C, 55.53; H, 4.73; N, 5.09.

EXAMPLE II

Preparation of
2-(2'-Chloro-4'-aminophenyl)-5,5-dimethyl-1,3-cyclohexanedione

A solution of 20.0 g (0.067 mol) of 2-(2'-chloro-4'-nitrophenyl)-5,5-dimethyl-1, 3-cyclohexanedione in 150 ml of concentrated ammonium hydroxide and 150 ml of ethanol was stirred at room temperature while passing hydrogen sulfide gas through the solution at such a rate that all of the $H_2S$ was absorbed. When the solution was saturated with $H_2S$, the temperature was raised to the reflux point and $H_2S$ continuously passed slowly through the refluxing solution for 24 hours. The reaction mixture was filtered to remove sulfur, and the filtrate evaporated under reduced pressure. To the residue was added 300 ml of 0.25 N NaOH, and the solution filtered once more. The filtrate was cooled and carefully acidified to pH=4 with 6 N HCl. 2-(2'-Chloro-4'-aminophenyl)-5,5-dimethyl-1, 3-cyclohexanedione was collected by suction filtration.

Yield: 13.3 g (74%), m.p. 218°–219° C.

Calculated for: $C_{14}H_{16}ClNO_2.\frac{1}{2}H_2O$. C, 61.20; H, 6.24; N, 5.10
Found: C, 60.44; H, 5.83; N, 5.32

EXAMPLE III

Preparation of 2-(2'-Chlorophenyl)-5,5-dimethyl-1, 3-cyclohexanedione 2-(2'-Chloro-4'-aminophenyl)-5,5-dimethyl-1, 3-cyclohexanedione (9.66 g, 0.0364 mol) was added to 7.0 ml of water, and the mixture stirred and heated almost to boiling. An additional 15.0 ml of HCl was added and the mixture cooled to 0°–5° C. A solution of 3.22 g (0.0467 mol) of sodium nitrite in 9.0 ml of water was added dropwise while the reaction mixture was stirred and maintained at 0°–5° C. When the addition of the sodium nitrite solution was complete, the reaction mixture was stirred at 0°–5° C. for one hour.

The diazonium salt solution prepared above was added in portions to 161 ml of 50% hypophosphorous acid at 0° C., with stirring and cooling. The reaction mixture was stirred for 12 hours and filtered to give 8.55 g of a tan solid. This material was chromatographed through 250 g of silica gel (0.063–0.2 mm) eluting with a gradient from pure benzene to 70:30 benzene-ethyl acetate. A total of 7.12 g of reaction product was obtained from the chromatography and recrystallized from benzeneacetate to give 6.85 g (75%) of 2-(2'-Chlorophenyl)-5,5-dimethyl-1, 3-cyclohexanedione as white crystals, m.p. 191°–192° C.

Calculated for $C_{14}H_{15}C_1O_2$: C, 67.07; H, 6.03
Found: C, 67.04; H, 6.00.

EXAMPLE IV

Preparation of 2-(2', 4'-Dichlorophenyl)-5,5-dimethyl-1, 3-cyclohexanedione

A fresh sample of cuprous chloride was prepared by slowly adding a solution of 2.09 g of sodium bisulfite and 1.38 g of NaOH in 20 ml of water to a solution of 9.86 g $CuSO_4.5 H_2O$ and 2.75 g NaCl in 100 ml of hot water. The suspension of CuCl was cooled to room temperature, and washed several times with water while exercising care to avoid exposure of the cuprous chloride to air.

A suspension of 5.00 g (0.0188 mol) of 2-(2'-chloro-4'-aminophenyl)-5,5-dimethyl-1, 3-cyclohexanedione in 75 ml of water containing 4.0 ml of concentrated HCl was stirred and heated almost to boiling for 10 min., then cooled to 10° C. and an additional 7 ml of conc. HCl added and the solution cooled to 0°–5° C. A solution of 2.00 g (0.0282 mol) of sodium nitrite in 6.0 ml of water was added dropwise to the amine hydrochloride solution while maintaining the temperature at 0°–5° C. When all the $NaNO_2$ solution had been added, the diazonium salt solution was stirred for 30 min. at 0° C.

The diazonium salt solution was added, in small portions to a solution of the cuprous chloride in 40 ml of conc. HCl at 0° C. When all of the diazonium salt solution had been added, the reaction mixture was stirred overnight at room temperature and filtered to give 6.22 g of a tan solid, m.p. 175°–178° C. This crude product was chromatographed through silica gel (0.063–0.2 mm) using a benzene-ethyl acetate gradient from pure benzene to 70:30 benzene-ethyl acetate to give 3.51 g (65%) of 2-(2',4'-Dichlorophenyl-5,5-dimethyl-1, 3-cyclohexanedione as a white, crystalline solid, m.p. 208.5°–210° C.

Calculated for: $C_{14}H_{14}Cl_2O_2$: C, 58.97; H, 4.95,
Found: C, 59.06; H, 4.82.

EXAMPLE V

Preparation of
2-(2',6'-Dichloro-4'-nitrophenyl)-5,5-dimethyl-1,3-cyclohexanedione A solution of 30.98 g (0.221 mol) of 5,5-dimethyl-1,3-cyclohexanedione and 76.36 g (0.553 mol) of anhydrous potassium carbonate in 300 ml of dimethylformamide was heated to 75° C. with stirring under $N_2$ for one hour. The 3,4,5-trichloronitrobenzene (50.0 g, 0.221 mol) was dissolved in 100 ml of dimethylformamide and added to the reaction mixture, while stirring and maintaining the temperature at 75° C. A deep red-colored solution was formed, and when the addition was complete the temperature was raised to 100° C. and the mixture stirred over night at this temperature. Most of the dimethylformamide was removed by vacuum distillation, and 21 of water was added to the residue. The aqueous solution was extracted three times with 500 ml portions of benzene, then $N_2$ was passed through the aqueous solution while warming to remove dissolved benzene. The solution was cooled in an ice bath and acidified with 6 N HCl to give 63.8 g (87%) of 2-(2',6'-dichloro-4'-nitrophenyl)-5,5-dimethyl-1,3-cyclohexanedione as a tan powder, m.p. 288°–290° C.

Calculated for $C_{14}H_{13}Cl_2NO_4$: C, 50.93; H, 3.97; N, 4.24

Found: C, 50.09; H, 3.79; N, 4.26

EXAMPLE VI

Preparation of 2-(2', 6'-Dichloro-4'-aminophenyl)-5,5-dimethyl-1,3-cyclohexanedione A solution of 20.0 g (0.0606 mol) of 2-(2',6'-dichloro-4'-nitrophenyl)-5,5-dimethyl-1,3-cyclohexanedione in 150 ml conc. $NH_4OH$ and 150 ml of ethanol was stirred at room temperature while passing $H_2S$ gas through the solution at such a rate that all of the $H_2S$ was absorbed. After the solution was saturated with $H_2S$, it was refluxed 24 hours while continuously passing $H_2S$ slowly through the solution. The reaction mixture was cooled to room temperature, the precipitated sulfur removed by filtration, and the filtrate evaporated to dryness under reduced pressure. To the residue was added 300 ml of 0.25 N NaOH, and the solution filtered once more. The filtrate was cooled and acidified to pH=4 with 6 N HCl. A tan solid formed which was collected by filtration to give 11.2 g when dry. This material was washed with methylene chloride to give 8.2 g (45%) of 2-(2',6'-dichloro-4'-aminophenyl)-5,5-dimethyl-1, 3-cyclohexanedione as a white powder, m.p. 243° d.

Calculated for $C_{14}H_{15}Cl_2NO_2$: C, 56.02; H, 5.04; N, 4.67,

Found: C, 56.34; H, 4.95; N, 4.67.

EXAMPLE VII

Preparation of 2-(2',6'-Dichlorophenyl)-5,5-dimethyl-1,3-cyclohexanedione

The 2-(2',6'-dichloro-4'-aminophenyl)-5,5-dimethyl-1,3-cyclohexanedione (5.00 g, 0.0167 mol) was added to 3.5 ml of concentrated HCl in 75 ml of water, and the mixture stirred and heated almost to boiling. The suspension was cooled to 10° C. and an additional 7.5 ml of conc. HCl was added. The mixture was cooled to 0°–5° C. and a solution of 1.44 g (0.0209 mol) of sodium nitrite in 3.5 ml. of water was added dropwise while the reaction mixture was stirred and maintained at 0°–5° C. When addition of the sodium nitrite solution was complete, the reaction mixture was stirred at 0° C. for one hour.

The diazonium salt solution prepared above was added in portions to 75 ml of 50% hypophosphorous acid at 0° C. with stirring and cooling. The reaction mixture was stirred for 2 hours and filtered to give 5.03 g of brown powder. This material was recrystallized from benzenechloroform to give 2.69 g of a light tan solid m.p. 227°–229° C. The residue from the mother liquor (1.70 g) was chromatographed through silica gel (0.063–0.2 mm) to give 0.84 g of a white solid, m.p. 228°–232° C. Total yield of 2-(2',6'-Dichlorophenyl)-5,5-dimethyl-1,3-cyclohexane-1,3-dione was 3.53 g (74%).

Calculated for $C_{14}H_{14}Cl_2O_2$: C, 58.97; H, 4.95,
Found: C, 58.64; H, 4.86.

EXAMPLE VIII

Preparation of 2-(2',4', 6'-Trimethylphenyl)-cyclohexane-1,3-dione

A solution of 5.00 g (0.036 mol) of 2-diazocyclohexane-1,3-dione in 500 ml of mesitylene (dry, distilled) containing 32.8 g (0.18 mol) benzophenone was degassed with nitrogen for one hour and irradiated with a 200 watt mercury arc lamp fitted with a borosilicate glass filter until the complete disappearance of the diazo band (4.68 u) in the infrared was observed. The reaction was also monitored by thin layer chromatography (90:10 ethyl acetate-benzene) and irradiation continued until no diazoketone at $R_f=0.31$ could be seen. The irradiation required 11 hours. The mesitylene was extracted with 0.25 N sodium hydroxide until a small aliquot showed no cloudiness upon acidification. The combined base extracts were washed twice with 200 ml portions of ether, and acidified (pH 3–5) with 1 N HCl. The aqueous solution was extracted three times with 75 ml portions of chloroform, dried over anhydrous $MgSO_4$, and the solvent stripped to give 5.06 g of a tan solid.

This solid was chromatographed through 250 g silica gel (0.063-0.2 mm) eluting with a gradient from pure benzene to 80:20 benzene-ethyl acetate. A total of 2.60 g (31%) of a white solid (homogeneous by thin layer chromatography) was obtained and recrystallized from diisopropyl ether to give 1.96 g of 2-(2',4',6'-Trimethylphenyl)cyclohexane-1,3-dione as white crystals, mp 196°–198° C.

Calculated for $C_{15}H_{18}O_2$: C, 78.23; H, 7.88,
Found: C, 77.94; H, 8.20.

EXAMPLES IX AND X

Preparation of 2-(2',4'-Dimethylphenyl)-5,5-dimethylcyclohexane-1,3-dione and 2-(2',6'-dimethylphenyl)-5,5-dimethylcyclohexane-1,3-dione A solution of 5.00 g (0.0301 mol.) of 2-diazo-5,5-dimethylcyclohexane-1,3-dione in 500 ml of m-xylene containing 27.4 g (0.15 mol) of benzophenone was degassed with nitrogen for one hour and irradiated overnight with a 200 watt mercury arc lamp fitted with a borosilicate glass filter. The photolysis mixture was extracted with 0.25 N NaOH, the combined base extracts washed with ether and acidified with chloroform, dried over anhydrous $mgSO_4$ and the solvent removed to leave 3.61 g of a tan solid. Irradiation was repeated using 7.00 g (0.042 mol) of 2-diazo-5,5-dimethylcyclohexane-1,3-dione and 38.38 g (0.21 mol) of benzophenone in 500 ml of m-xylene. Workup gave 5.48 g of tan solid.

The combined crude products (9.09 g) were chromatographed through silica gel (0.063–0.2 mm) using benzene-ethyl acetate as eluent. The column was eluted with (1) 500 ml benzene (2) 500 ml of 95.5 benzene-ethyl acetate (3) 1000 ml of 90:10 benzene-ethyl acetate and (4) 1000 ml of 80:20 benzene-ethyl acetate. After collecting 2 liters of solvent, the column was attached to an automatic fraction collector and 15 ml fractions collected. Tubes 1–94 contained small amounts of a yellow oil. Tubes 95-150 contained a light yellow solid which showed one component ($R_f$ 0.55 in 50:50 hexane-ethyl acetate) by thin layer chromatography and weighed 2.18 g. This material was recrystallized from benzene to give 1.17 g of 2-(2',4'-Dimethylphenyl)-5,5-dimethyl-1,3-cyclohexanedione as a white powder, mp 167°–169° C.

Calculated for: $C_{16}H_{20}O_2$: C, 78.65; H, 8.25
Found: C, 78.68; H, 8.12.

This compound was shown to be 2-(2',4'-dimethylphenyl)-5, 5-dimethyl-1,3-cyclohexanedione.

Tubes 151–230 were combined to give 2.0 g of white solid showing one component ($R_f$ 0.57 in 50:50 hexane-ethyl acetate by thin layer chromatography. This material was recrystallized from benzene to give 1.90 g of 2-(2',6'-Dimethylphenyl)-5,5-dimethyl-1, 3-cyclohexanedione as white crystals, mp 177°–186° C.

Calculated for: $C_{16}H_{20}O_2$: C, 78.65; H, 8.25,
Found: C, 78.28; H, 8.21.

This compound was shown to be 2-(2',6'-Dimethylphenyl)-5,5-dimethyl-1, 3-cyclohexanedione.

EXAMPLE XI

Preparation of 2-Diazo-5-phenylcyclohexane-1,3-dione

A solution of 20.0 g (0.106 mol) of 5-phenylcyclohexane-1,3-dione in 75 ml ethanol was cooled to −10° C. and stirred magnetically under nitrogen. To the mixture was added 10.75 g (0.106 mol) of triethylamine. The tosyl azide (20.95 g 0.106 mol) was added all at once, and the mixture stirred for one hour at C–5° C. The solvent was removed under vacuum at a temperature less than 40° C. To the residue was added 200 ml ether, and the mixture extracted with a solution containing 3.1 g potassium hydroxide in 200 ml of water. The ethereal solution was dried over anhydrous $MgSO_4$ filtered and the solvent removed to give a yellow solid which was recrystallized from ethanol-hexane to give 8.38 g (32%) of 2-diazo-5-phenylcyclohexane-1,3-dione as yellow crystals, mp 122°–124° C.

EXAMPLE XII

Preparation of 2-(2',4',6'-Trimethylphenyl)-5-phenylcyclohexane-1,3-dione

A solution of 7.0 g (0.0327 mol) of 2-diazo-5-phenylcyclohexane-1,3-dione and 29.77 g (0.163 mol) of benzophenone in 500 ml of mesitylene was degassed for one hour with nitrogen and irradiated with a 200 watt mercury arc lamp fitted with a borosilicate glass filter overnight. The photolysis mixture was extracted with 0.25 N sodium hydroxide, the combined base extracts washed with ether, acidified with 1 N HCl, and extracted with chloroform. The chloroform solution was dried over anhydrous $MgSO_4$, and the solvent stripped to give 5.7 g of tan solid. This material was purified by column chromatography on silica gel (0.063–0.2 mm) using benzene-ethyl acetate to give 5.7 g (57%) of a white solid. This was recrystallized from benzene-ethyl acetate to give 4.08 g (41%) of 2-(2',4',6'-Trimethylphenyl)-5-phenylcyclohexane-1,3-dione as a white crystalline solid, mp. 215°–216° C.

Calculated for: $C_{21}H_{22}O_2$: C, 82.32; H, 7.24,
Found: C, 82.38; H, 7.14.

EXAMPLE XIII

Preparation of 2-(2',6'-Dimethyl-4'-t-butylphenyl)-5,5-dimethyl-1,3-cyclohexanedione A solution of 7.00 g (0.042 mol) of 2-diazo-5, 5-dimethylcyclohexane-1,3-dione in 300 ml of 5-t-butyl-m-xylene and 250 ml chlorobenzene containing 38.38 g (0.21 mol) of benzophenone was irradiated overnight with a 200 watt mercury arc lamp fitted with a borosilicate glass filter after degassing for 1 hour under nitrogen. The photolysis mixture was extracted with 0.25 N NaOH, washed with ether, acidified with 1 N HCl, and extracted with chloroform. The chloroform was dried over anhydrous $MgSO_4$ and stipped to give a crude yellow solid. The photolysis was repeated and the combined crude product from these reactions was chromatographed through silica gel (0.063–0.2 mm) using benzene-ethyl acetate. The solid obtained from the chromatography was recrystallized from benzene to give 2.76 g (11%) of 2-(2',6'-dimethyl-4'-t-butylphenyl)-5,5-dimethyl-1 3-cyclohexanedione as white crystals, mp 244°–49° C.

Calculated for: $C_{20}H_{28}O_2$: C, 79.95; H, 9.39,
Found: C, 79.76; H, 9.45.

EXAMPLE XIV

Preparation of 2-Diazodecalin-1,3-dione

A solution of 10.0 g (0.0768 mol) of decalin-1,3-dione in 50 ml of ethanol was magnetically stirred under nitrogen and cooled to −10° C. To the solution was added 7.77 g (0.0768 mol) of triethylamine followed by 15.14 g (0.0768 mol) of p-toluenesulfonylazide added all at once. The mixture was stirred for one hour at 0° C., and the solvent removed at reduced pressure at a temperature of less than 40° C. To the residue was added 200 ml of ether, and the ether removed to yield a yellow solid. This was recrystallized from ethanol to give 5.23 g of yellow crystals, mp 81°–83° C.

EXAMPLE XV

Preparation of 2-(2'-Methylphenyl)-decalin-1,3-dione

A solution of 7.0 g (0.0364 mol) of 2-diazodecalin-1,3-dione and 33.18 g (0.182 mol) of benzophenone in 500 ml of toluene was degassed for one hour with nitrogen and irradiated with a 200 watt mercury arc lamp fitted with a borosilicate glass filter overnight. The photolysis mixture was extracted with 0.25 N NaOH, the combined base extracts washed with ether, acidified with 1 M HCl and extracted with chloroform. The chloroform extracts were dried over anhydrous $MgSO_4$, and the solvent removed to give 4.56 g of a yellow crude product. This was purified by column chromatography through silica gel (0.063–0.2 mm) with benzene-ethyl acetate. The solid obtained was recrystallized from benzene to give 1.85 g (20%) of 2-(2'-Methylphenyl)-decalin-1,3-dione as white crystals, mp 165°–167° C.

Calculated for: $C_{17}H_{20}O_2$: C, 79.65; H, 7.86,
Found: C, 79.82; H, 7.43.

EXAMPLE XVI

Preparation of Ethyl 6-(2',4'-Dimethylphenyl)-6-cyano-5-keto-3,3-dimethyl-hexanoate A clean, dry 500 ml 3-neck flask was equipped with a reflux condenser, mechanical stirrer, addition funnel and nitrogen inlet. The flask was charged with 70 ml of absolute ethanol followed by 6.00 g (0.26 g-atom) of sodium, and the reaction mixture stirred and heated until all the sodium had dissolved. The temperature of the reaction mixture was then raised to the reflux point, and a mixture of 29.04 g (0.20 mol) of 2,4-dimethylbenzyl cyanide and 64.88 g (0.30 mol) of diethyl 3,3-dimethyl glutarate added, dropwise, over a 2 hour period through the addition funnel. When the addition was complete, the reaction mixture was maintained at reflux for 12 hrs. At the end of this time, approximately ⅔ of the ethanol was distilled off, and the reaction mixture refluxed for 2 hrs. more, then cooled to room temperature and poured into 600 ml of an ice water mixture.

The basic aqueous solution was extracted twice with 300 ml of ether, and then acidified (pH=3) with 6 N HCl. An oil formed, and the aqueous acid solution was extracted twice with 250 ml portions of ether. The ether phase from the extraction of the aqueous acid was washed twice with water, dried over anhydrous $MgSO_4$, and stripped to leave 52.83 g (84%) of ethyl 6-(2',4'-Dimethylphenyl)-6-cyano-5-keto-3,3-dimethylhexanoate as a clear, colorless, very viscous oil. This oil was not purified, but was characterized by infrared and nuclear magnetic resonance spectrometry.

IR (neat, $\mu$, principal absorptions): 2.8–3.2 (OH, enol); 4.55 (C≡N); 5.85, 6.02, 6.19 (C=O); 6.3 (C=C); 7.45, 8.25, 9.85, 12.25.

NMR ($CDCl_3$, $\delta$): 1.20 (multiplet, 9H); 2.33 (multiplet, 8H); 2.68 (multiplet, 2H); 4.17 (quartet, 2H): 4.90 and 12.0 (singlet, 1H); 7.05 (multiplet, 3H).

EXAMPLE XVII

Preparation of 2-(2',4'-Dimethylphenyl)-5,5-dimethyl-1,3-cyclohexanedione and 6-(2',4'-Dimethylphenyl)-5-keto-3,3-dimethylhexanoic acid A one-neck round bottom flask was charged with 52.50 g (0.17 mol) of ethyl 6-(2',4'-dimethylphenyl)-6-cyano-3,3-dimethylhexanoate, 250 ml of concentrated hydrochloric acid, 250 ml of glacial acetic acid, and 100 ml of water. The reaction mixture was stirred and refluxed for 48 hours. After 12 hours and 24 hrs. of refluxing, an additional 100 ml of conc. HCl and 100 ml glacial HOAC were added. After 48 hours, the mixture was stripped to dryness under reduced pressure. To the residue were added 150 ml of water and 150 ml of ethyl ether, and the mixture shaken vigorously. A white, crystalline precipitate formed, and this was removed by suction filtration to give 13.20 g (32%) of 2-(2',4'-Dimethylphenyl)-5,5-dimethyl-1,3-cyclohexanedione as a white, crystalline solid, m.p. 167°–168.5° C.

Calcd. for $C_{16}H_{20}O_2$: C, 78.65; H, 8.25;
Found: C, 78,68; H, 8.12.

The ether layer was separated from the filtrate, washed once with water, dried over anhydrous $MgSO_4$ and stripped to give 29.04 g (65%) of 6-(2',4'-dimethylphenyl)-5-keto-3,3-dimethylhexanoic acid as a viscous yellow oil. This oil was not purified, but was characterized by infrared and nuclear magnetic resonance spectrometry.

IR ($CHCl_3$, $\mu$, principal absorptions): 2.9–4.3 (OH); 5.90 (C=O)

NMR ($CDCl_3$, $\delta$): 1.10 (singlet, 6H); 2.20 singlet, 3H); 2.30 (singlet, 3H); 2.50 (singlet, 2H); 2.62 (singlet, 2H); 3.70 (singlet, 2H); 7.08 (singlet, broad, 3H).

EXAMPLE XVIII

Preparation of 2-(2'-Chlorophenyl)-1,3-cyclohexanedione

A 500 ml round bottom flask was charged with 10.0 g (0.0416 mol) of 6-(2'-chlorophenyl)-5-ketohexanoic acid and 100 ml of 72% sulfuric acid. The reaction mixture was stirred and heated to 120° C. for 5½ hours (oil bath), then poured into 600 ml of an ice water mixture. A tacky, white solid formed, and this was extracted into 300 ml of methylene chloride. The $CH_2Cl_2$ solution was washed six times with water, dried over anhydrous $MgSO_4$ and stripped to leave 8.87 g of a tacky, white solid. This material was recrystallized from ethyl acetate to give 5.85 g (63%) of 2-(2'-chlorophenyl)-1,3-cyclohexanedione as a white, crystalline solid, m.p. 148.5°–149° C.

Calculated for $C_{12}H_{11}ClO_2$: C, 64.73; H, 4.98;
Found: C, 64.49; H, 4.89.

EXAMPLE XIX

Preparation of 6-(2',4'-Dimethylphenyl)-5-ketohexanoic acid

Utilizing the procedure of EXAMPLE XVII ethyl 6-(2',4'-dimethylphenyl)-6-cyano-5-ketohexanoate was hydrolyzed in the presence of concentrated hydrochloric acid to prepare 6-(2',4'-dimethylphenyl)-5-ketohexanoic acid in 49% yield as a tan solid, m.p. 75.0°–76.5° C. This solid was characterized by infrared and nuclear magnetic resonance spectrometry.

IR ($CHCl_3$, $\mu$ principle absorptions): 2.9–4.2 (OH); 5.92 (C=O);

NMR ($CDCl_3$, $\delta$): 1.7–3.3 (multiplet, 6H); 2.48 (singlet 3H); 3.71 (singlet, 2H); 7.31 (singlet, broad, 3H).

EXAMPLE XX

Preparation of Ethyl 6-(2',4'-Dimethylphenyl)-5-ketohexanoate

A 500 ml one-neck round bottom flask equipped with a Soxhlet extraction apparatus containing 100 g of molecular sieves having a pore size of 3A was charged with 12.74 g (0.0544 mol) of 6-(2',4'-dimethylphenyl)-5-ketohexanoic acid, 125 ml of absolute ethanol, 125 ml of dry benzene, and 2.0 ml of concentrated sulfuric acid. The mixture was refluxed for 12 hours, then ⅔ of the ethanolbenzene removed under reduced pressure. The residue was poured into 500 ml of ice water, and extracted into 300 ml of ether. The ether was washed three times with 10% $K_2CO_3$, then once with water, dried over anhydrous $MgSO_4$, and removed to leave 13.34 g of a dark yellow oil. This was distilled to give 12.77 g (89%) of ethyl 6-(2',4'-Dimethylphenyl)-5-ketohexanoate as a clear, colorless oil, b.p. 133°–145° C. (0.05 mm). This oil was further characterized by infrared and nuclear magnetic resonance spectrometry.

IR (neat, $\mu$, principal absorptions): 5.85 (C=O), 8.60 (C=O).

NMR ($CDCl_3$, $\delta$): 1.15 (triplet, 3H); 1.50–2.6 (multiplet, 6H); 2.10 (singlet, 3H); 2.20 (singlet, 3H; 3.52 (singlet, 2H); 3.95 (quartet, 2H); 6.80 (singlet, broad, 3H).

EXAMPLE XXI

Preparation of 2-(2',4'-Dimethylphenyl)-1,3-cyclohexanedione

A 500 ml 3-neck round bottom flask was equipped with a mechanical stirrer, addition funnel, and reflux condenser. The glassware was dried thoroughly and the flask charged with 4.62 g (0.096 g-atoms) of 50% sodium hydride in mineral oil. The oil was washed off the NaH using toluene, and then 100 ml of toluene added. The mixture was warmed to 65° C. and 12.62 g (0.0481 mol) of ethyl 6-(2',4'-dimethylphenyl)-5-ketohexanoate added, dropwise, over a 2 hr. period. The mixture was maintained at 65° C. for 12 hrs., then carefully quenched with 25 ml of ice water. The reaction mixture was diluted with 250 ml of water and extracted twice with 150 ml of ether. The aqueous base solution was acidified to pH=3 with 6 N HCl, and extracted twice with 150 ml of methylene chloride. The methylene chloride was washed with water, dried over anhydrous $MgSO_4$, and stripped to give 5.88 g of a semisolid. This was recrystallized from ethyl acetate to give 5.10 g (49%) of 2-(2',4'-Dimethylphenyl)-1,3-cyclohexanedione as a white, crystalline solid, m.p. 143°–145° C.

Calculated for: $C_{14}H_{16}O_2$: C, 77.75; H, 7.46,
Found: C, 76.99; H, 7.46.

EXAMPLE XXII

Preparation of Ethyl 6-(2',5'-Dimethylphenyl)-6-cyano-5-keto-3,3-dimethylhexanoate Utilizing the procedure of EXAMPLE XVI, 29.04 g (0.200 mol) of 2,5-dimethylbenzyl cyanide and 64.88 g (0.300 mol) of diethyl 3,3-dimethyl glutarate were reacted to yield 45.24 g (72%) of ethyl 6-(2',5=-dimethylphenyl)-6-cyano-5-keto-3,3-dimethylhexanoate as a clear, colorless viscous oil. Structure was confirmed by infrared and nuclear magnetic resonance spectrometry.

IR (neat, $\mu$, principal absorptions): 2.9–3.7 (OH, emol); 4.55 (C≡N); 5.80, 5.98, 6.10 (C=O); 6.23 (C=C); 7.35; 7.60; 8.15; 9.70; 12.30.

NMR ($CDCl_3$, $\delta$): 1.18 (multiplet, 9H); 1.67–2.73 (multiplet, 10H); 4.12 (quartet, 2H); 4.88 (singlet 1H); 7.05 (broad, singlet, 3H).

EXAMPLE XXIII

Preparation of 6-(2',5'-Dimethylphenyl)-5-keto-3,3-dimethylhexanoic acid and 2-(2',5'-Dimethylphenyl)-5,5-dimethyl-1,3-cyclohexanedione A solution of 45.24 g (0.14 mol) of ethyl 6-(2',5'-Dimethylphenyl)-6-cyano-5-keto-3,3-dimethylhexanoate, 250 ml of glacial acetic acid, 250 ml of concentrated HCl, and 70 ml of water was refluxed for 48 hours. After 24 hours, an additional 100 ml of concentrated HCl and 150 ml of glacial acetic acid were added.

After 48 hours of refluxing, the reaction mixture was cooled to room temperature and the solvent removed under reduced pressure. The residue was shaken vigorously with 250 ml of water and 250 ml of diisopropyl ether. A white, crystalline precipitate formed which was removed by suction filtration to give 7.90 g (23% yield) of 2-(2',5'-dimethylphenyl)-5,5-dimethyl-1,3-cyclohexanedione m.p. 168°–170° C.

Calculated for $C_{16}H_{20}O_2$: C, 78.65; H, 8.25;
Found: C, 78.16; H, 8.03.

The ether layer was separated from the filtrate, washed once with water, dried over anhydrous $MgSO_4$, and stripped to give 17.97 g of 6-(2',5'-Dimethylphenyl)-5-keto-3,3-dimethyl hexanoic acid as a yellow oil. This oil was not purified, but was characterized by infrared and nuclear magnetic resonance spectrometry.

IR (neat, $\mu$, principal absorptions): 2.9–3.8 (OH); 5.90 (C=O); 12.3 (aromatic)

NMR ($CDCl_3$, $\delta$): 1.08 (singlet, 6H); 2.03 (singlet, 2H); 2.13 (singlet, 2H); 2.27 (singlet, 3 H); 2.33 (singlet, 3H); 7.0 (singlet, 3H).

EXAMPLE XXIV

Preparation of Ethyl 6-(2',5'-dimethylphenyl)-5-keto-3,3-dimethylhexanoate

Utilizing the procedure of EXAMPLE XX 6-(2',5'-dimethylphenyl)-5-keto-3,3-dimethyl hexanoic acid was esterified with absolute ethanol in the presence of a catalytic amount of concentrated sulfuric acid to provide 15.52 g (78% yield) of ethyl 6-(2',5'-dimethylphenyl)-5-keto-3,3-dimethylhexanoate as a pale viscous oil.

EXAMPLE XXV

Preparation of 2-(2',5'-Dimethylphenyl)-5,5-dimethyl-1,3-cyclohexanedione

Utilizing the procedure of EXAMPLE XXI, 6-(2',5'-dimethylphenyl-5-keto-3,3-dimethylhexanoate was treated with sodium hydride to yield 9.87 of crude product, which on recrystallization yielded 8.77 g (64%) of 2-(2',5'-dimethylphenyl)-5,5-dimethyl-1,3-cyclohexanedione as a white, crystalline solid m.p. 167°–168° C.

EXAMPLE XXVI

Preparation of 3-(2-Ethylhexanoyloxy)-2-(2'-chlorophenyl)-5,5-dimethyl-2-cyclohexenone A solution of 1.009 (3.99 mmol) of 2-(2'-chlorophenyl)-5,5-dimethyl-1,3-cyclohexanedione and 0.03 g (8.0 mmol) of pyridine was cooled in an ice bath and stirred under $N_2$. The 2-ethylhexanoyl chloride (0.69 g, 4.25 mmol) was added, the mixture was then allowed to warm to room temperature, stirred at room temperature for one hour and refluxed for one hour. The solvent was removed under reduced pressure and the residue taken up in ether and water.

The ether was washed three times with 0.25 N HaOH, three times with 10% HCl and with water. The ether was dried over anhydrous $MgSO_4$ and decanted to give 1.23 g (82%) of 3-(2'-ethylhexanoyloxy)-2-(2'-chlorophenyl)-5,5-dimethyl-2-cyclohexenone as a clear colorless oil which was homogeneous by thin layer chromatography.

Calculated for $C_{22}H_{29}ClO_3$: C, 70.10; H, 7.76;
Found: C, 70.09; H, 7.86.

EXAMPLE XXVII

Preparation of 3-(2'-Ethylhexanoyloxy)-2-(2',4'-dichlorophenyl)-5,5-dimethyl-2-cyclohexenone A solution of 1.76 g (7.02 mmol) of 2-(2',4'-dichlorophenyl)-5,5-dimethyl-1,3-cyclohexanedione in 10 ml of chloroform was cooled in ice and 1.11 g (14.04 mmol) of pyridine added followed by 1.21 g (7.47 mmol) of 2-ethylhexanoyl chloride. The mixture was stirred for 2 hrs. at room temperature and then refluxed for 12 hrs.

The reaction mixture was worked up exactly as described for Example I above to give 2.09 g of a yellow oil. This material was chromatographed using low pressure liquid chromatography on silica gel with a hexane-ethyl acetate gradient to give 1.15 g (41%) of 3-(2'- ethylhexanoyloxy)-2-(2',4'-dichlorophenyl)-5,5-dimethyl-2-cyclohexenone as a clear, colorless oil. The thin layer chromatogram (80:20 hexane-ethyl acetate) of this material showed one spot at Rf=0.46.

Calculated for $C_{22}H_{28}Cl_2O_3$: C, 64.23; H, 6.86;
Found: C, 64.44; H, 6.80.

EXAMPLE XXVIII

Preparation of 3-hexanoyloxy-5,5-dimethyl-2-(2',4'-dimethylphenyl)-2-cyclohexenone A solution of 1.50 g (6.14 mmol) of 2-(2',4'-dimethylphenyl)-5,5-dimethyl-1,3-cyclohexanedione in 10 ml of chloroform was cooled in ice and 1.94 g (24.56 mmol) of pyridine added followed by 1.64 g (12.28 mmol) of hexanoyl chloride. The mixture was stirred for 2 hrs. at room temperature, then refluxed for 5 hrs.

The reaction mixture was cooled to room temperature and taken up in 150 ml of ether. The ether was washed three times with 50 ml of 0.25 N NaOH, twice with 50 ml portions of ice cold 6 N HCl, and twice with water. The ether was dried over anhydrous ($MgSO_4$) and removed under reduced pressure to leave 0.98 g (47% yield) 3-hexanoyloxy-5,5-dimethyl-2-(2',4'-dimethylphenyl)-2-cyclohexenone as a clear, colorless oil. This oil showed one spot on a thin layer chromatogram (70:30 hexane-ethyl acetate) at Rf=0.49.

Calculated for $C_{22}H_{30}O_3$: C, 77.15; H, 8.83;
Found: C, 77.25; H, 8.92.

EXAMPLE XXIX

Preparation of 3-(2-Ethylhexanoyloxy)-5,5-dimethyl-2-(2',4'-dimethylphenyl)-2-cyclohexenone A solution of 1.50 g (6.14 mmol) of 2-(2',4'-dimethylphenyl)-5,5-dimethyl-1,3-cyclohexanedione in 10 ml of chloroform was cooled in ice and 1.94 g (24.56 mmol) of pyridine added followed by 2.00 g (12.28 mmol) of 2-ethylhexanoyl chloride. The mixture was stirred for 2 hrs. at room temperature, then refluxed for 12 hrs. The mixture was worked up exactly as described in Example I above to give 1.58 g of a slightly yellow, viscous oil. This material was chromatographed through 75 g of silica gel (0.063–0.2 mm) using a gradient ranging from 98:2 to 90:10 hexane-ethyl acetate. The chromatography gave 1.15 g (51%) of 3-(2-ethylhexanoyloxy)-5,5-dimethyl-2-(2',4'-dimethylphenyl)-2-cyclohexenone as a clear colorless oil which showed one spot on a thin layer chromatogram (70:30 hexane-ethyl acetate) at Rf=0.52.

Calculated for: $C_{24}H_{34}O_3$: C, 77.80; H, 9.25;
Found: C, 77.34; H, 9.48.

EXAMPLE XXX

Preparation of 3-Hexanoyloxy-2-(2',4'-dichlorophenyl)-5,5-dimethyl-2-cyclohexenone A solution of 2.00 g (8.00 mmol) of 2-(2',4'-dichlorophenyl)-5,5-dimethyl-1,3-cyclohexanedione in 10 ml of chloroform was cooled in ice and 1.26 g (16.00 mmol) of pyridine was added followed by 1.14 g (8.50 mmol) of hexanoyl chloride. The mixture was stirred for 2 hrs. at room temperature and refluxed for 12 hrs.

The reaction mixture was worked up exactly as described for Example I above to give 1.94 g of a slightly yellow oil. This material was chromatographed using a low pressure liquid chromatography system and a hexane-ethyl acetate gradient. Work-up of the chromatography gave 1.55 g (51% yield) of 3-hexanoyloxy-2-(2',4'-dichlorophenyl)-5,5-dimethyl-2-cyclohexenone as a clear, colorless oil which on a thin layer chromatogram (80:20 hexane-ethyl acetate) showed one spot at Rf=0.27.

Calculated for: $C_{20}H_{24}Cl_2O_3$: C, 62.67; H, 6.31;
Found: C, 62.83; H, 6.32.

EXAMPLE XXXI

Preparation of 3-(2-Ethylhexanoyloxy)-5,5-dimethyl-2-(2',5'-dimethylphenyl)-2-cyclohexenone A suspension of 1.50 g (6.14 mmol) of 2-(2',5'-dimethylphenyl)-b 5,5-dimethyl-1,3-cyclohexanedione in 15 ml of dry benzene was prepared and 0.49 g (7.37 mmol) of 85% powdered potassium hydroxide was added, followed by 1 drop of dicyclohexyl-18-crown-6-ether. After stirring for 30 minutes, 1.20 g (7.37 mmol) of 2-ethylhexanoyl chloride was added, and the reaction mixture refluxed for 12 hrs. The reaction mixture was cooled to room temperature, taken up in 150 ml ether and 50 ml of water, washed three times with 0.25 N NaOH, two times with water, two times with 6 N HCl, and once more with water. The ether solution was dried and stripped to leave 2.10 g (92% yield) of 3-(2-ethylhexanoyloxy)-5,5-dimethyl-2-(2',5'-dimethylphenyl)-2-cyclohexenone as a clear, colorless oil.

Calculated for: $C_{24}H_{34}O_3$: C, 77.80; H, 9.25;
Found: C, 77.46, H, 8.98.

EXAMPLE XXXII

Preparation of 2-(2',4'-Dimethylphenyl)-1,3-cyclohexanedione

A 500 ml 3-neck round bottom flask was equipped with a mechanical stirrer, addition funnel, and reflux condenser. The glassware was dried thoroughly and the flask charged with 4.62 g (0.096 g-atom) of 50% sodium hydride in mineral oil. The oil was washed off the NaH using toluene, and then 100 ml of toluene added. The mixture was warmed to 65° C. and 12.62 g (0.0481 mol) ethyl 6-(2',4' dimethylphenyl)-5-ketohexanoate added, dropwise, over a 2 hr. period. The mixture was maintained at 65° C. for 12 hrs., then carefully quenched with 25 ml of ice water. the reaction mixture was diluted with 250 ml of water and extracted twice with 150 ml of ether. The aqueous base solution was acidified to pH=3 with 6 N HCl, and extracted twice with 150 ml of methylene chloride. The methylene chloride was washed with water, dried over anhydrous $MgSO_4$ and stripped to give 5.88 g of a semi-solid. This was recrystallized from ethyl acetate to give 5.10 g (49%) of 2-(2',4'-dimethylphenyl)-1,3-cyclohexanedione as a white, crystalline solid, m.p. 143°–145° C.

Calculated for: $C_{14}H_{16}O_2$: C, 77.75; H, 7.46;
Found: C, 76.99; H, 7.46.

EXAMPLE XXXIII

Preparation of 2-(2'-Chlorophenyl)-1,3-cyclohexanedione

A 500 ml one-neck round bottom flask was charged with 10.0 g (0.0416 mol) of 6-(2'-chlorophenyl)-5-ketohexanoic acid and 100 ml of 72% sulfuric acid. The reaction mixture was stirred and heated to 120° C. for 5 ½ hrs. (oil bath) then poured into 600 ml of ice water. A tacky, white solid formed, and this was extracted into 300 ml of methylene chloride. The $CH_2Cl_2$ solution was washed six times with water, dried over anhydrous $MgSO_4$, and stripped to leave 8.87 g of a tacky, white solid. This material was recrystallized from ethyl acetate to give 5.85 g (63%) of 2-(2'-Chlorophenyl)-1,3-cyclohexanedione as a white, crystalline solid, m.p. 148.5°–149° C.

Calculated for: $C_{12}H_{11}ClO_2$: C, 64.73; H, 4.98;
Found: C, 64.49; H, 4.89.

EXAMPLE XXXIV

Preparation of 2-(2'-Chloro-4'-nitrophenyl)-5,5-dimethyl-1,3-cyclohexanedione A solution containing 42.05 g (0.300 mol) of 5,5-dimethyl-1, 3-cyclohexanedione and 100 g (0.718 g-atom) of anhydrous potassium carbonate in 300 ml of dry dimethylformamide was heated to 75° C. under nitrogen and stirred for one hour. The 3,4-dichloronitrobenzene, 57.60 g (0.300 mol) was dissolved in 100 ml dimethylformamide and added dropwise to the reaction mixture while stirring and maintaining the temperature of the reaction mixture at 75° C. A deep red-colored solution formed, and when the addition was complete the reaction temperature was raised to 100° C. and held at this temperature for 3 hours. Most of the dimethylformamide was removed by vacuum distillation. The residue was poured into 2l of ice water and extracted three times with 500 ml of benzene. Nitrogen was then passed through the aqueous solution while warming to remove dissolved benzene. The aqueous solution was cooled in an ice bath and acidified to give a tacky precipitate, which, upon warming solidified and was collected by suction filtration. The reaction product was recrystallized from acetone to give 31.7 g (36%) of 2-(2'-Chloro-4'-nitrophenyl)-5,5-dimethyl-1, 3-cyclohexanedione as a white powder, m.p. 250°–253° C.

Calculated for: $C_{14}H_{14}Cl\ NO_4.\frac{1}{2}\ H_2O$: C, 55.18 H, 4.96; N, 4.60;
Found: C, 55.53; H, 4.73; N, 5.09.

EXAMPLE XXXV

Preparation of 2-(2'-Chloro-4'-aminophenyl)-5,5-dimethyl-1,3-cyclohexanedione A solution of 20.0 g (0.067 mol) of 2-(2'-chloro-4'-nitrophenyl)-5,5-dimethyl-1,3-cyclohexanedione in 150 ml of concentrated ammonium hydroxide and 150 ml of ethanol was stirred at room temperature while passing hydrogen sulfide gas through the solution at such a rate that all of the $H_2S$ was absorbed. When the solution was saturated with $H_2S$, the temperature was raised to the reflux point and $H_2S$ continuously passed slowly through the refluxing solution for 24 hours. The reaction mixture was filtered to remove sulfur, and the filtrate evaporated under reduced pressure. To the residue was added 300 ml of 0.25 N NaOH, and the solution filtered once more. The filtrate was cooled and carefully acidified to pH=4 with 6 NHCl. A white solid formed which was collected by suction filtration to give 13.3 g (74%) of 2-(2'-Chloro-4'-aminophenyl)-5,5-dimethyl-1, 3-cyclohexanedione, m.p. 218°–219° C.

Calculated for: $C_{14}H_{16}Cl\ NO_2.\frac{1}{2}\ H_2O$: C, 61.20; H, 6.24; N, 5.10;
Found: C, 60.44; H, 5.83; N, 5.32.

EXAMPLE XXXVI

Preparation of 2-(2'-Chlorophenyl)-5,5-dimethyl-1,3-cyclohexanedione

The 2-(2'-chloro-4'-aminophenyl)-5,5-dimethyl-1,3-cyclohexanedione (9.66 g. 0.0364 mol) was added to 7.0 ml of concentrated HCl in 150 ml of water, and the mixture stirred and heated almost to boiling. An additional 15.0 ml of HCl was added and the mixture cooled to 0°–5° C. A solution of 3.22 g (0.0467 mol) of sodium nitrite in 9.0 ml of water was added dropwise while the reaction mixture was stirred and maintained at 0°–5° C. When addition of the sodium nitrite solution was complete, the reaction mixture was stirred at 0°–5° C. for one hour.

The diazonium salt solution prepared above was added in portions to 161 ml of 50% hypophosphorous acid at 0° C., with stirring and cooling. The reaction mixture was stirred for 12 hours and filtered to give 8.55 g of a tan solid. This material was chromatographed through 250 g of Woelm silica gel (0.063–0.2 mm) eluting with a gradient from pure benzene to 70:30 benzene-ethyl acetate. A total of 7.12 g of product was obtained from the chromatography and recrystallized from benzene-ethyl acetate to give 6.85 g (75%) of 2-(2'-Chlorophenyl)-5,5-dimethyl-1,3-cyclohexanedione as white crystals, m.p. 191°–192° C.

Calculated for: $C_{14}H_{15}ClO_2$: C, 67.07; H, 6.03;
Found: C, 67.04; H, 6.00.

EXAMPLE XXXVII

Preparation of 2-(2',4'-6'-Trimethylphenyl)-cyclohexane-1,3-dione

A solution of 5.00 g (0.036 mol) of 2-diazocyclohexane-1,3-dione in 500 ml of mesitylene (dry, distilled) containing 32.8 g (0.18 mol) benzophenone was degassed with nitrogen for one hour, and irradiated with a 200 watt Hanovia immersion lamp through a borosilicate glass filter, until the complete disappearance of the diazo band (4.68u) in the infrared was observed. The reaction was also monitored by thin layer chromatography (90:10 ethyl acetate-benzene) and irradiation continued until no diazoketone at $R_f=0.31$ could be seen. The irradiation required 11 hours. The mesitylene was extracted with 0.25 N sodium hydroxide until a small aliquot showed no cloudiness upon acidification. The combined base extracts were washed twice with 200 ml of ether, and acidified (pH=5) with 1 N HCl. The aqueous solution was extracted three times with 75 ml portions of chloroform, dried over anhydrous $MgSO_4$, and the solvent stripped to give 5.06 g of a tan solid.

This solid was chromatographed through 250 g of silica gel (0.065–1.2 mm) eluting with a gradient from pure benzene to 80:20 benzene-ethyl acetate. A total of 2.60 g (31%) of a white solid (homogeneous by thin layer chromatography) was obtained and recrystallized from diisopropyl ether to give 1.96 g of 2-(2',4',6'-trimethylphenyl)-1,3-cyclohexanedione as white crystals, mp 196°–198° C.

Calculated for: $C_{15}H_{18}O_2$: C, 78.23; H, 7.88;
Found: C, 77.94; H, 8.20.

EXAMPLE XXXVIII

Use of 3-(2-Ethylhexanoyloxy)-5,5-dimethyl-2-(2',4'-Dimethylphenyl)-2-cyclohexenone for the Control of Dermacentor variabis, Amblyama Maculatum and Amblyamma Americanum Six crossbred sheep of uniform age and health were used to evaluate 3-(2-ethylhexanoyloxy)-5,5-dimethyl-2-(2',4'-dimethylphenyl)-2-cyclohexenone at rates of 2, 5, 7 and 10 mg/kg/day.

Plastic corkscrew-type cannalas (Kaver-Lockhart Laboratories, Shaunee Mission, Kansas, were inserted through the abdominal and rumen walls to provide direct access to the rumen. The diameter of the fistula was reduced from 10 to 7 mm. by threading latex rubber tubing (12 mm OD) through the cannula. The latex tubing extended 4 cm externally to allow a tubing clamp to constrict the outer orifice. 3-(2-Ethylhexanoyloxy)-5,5-dimethyl-5,5-dimethyl-2(2',4'-dimethylphenyl)-2-cyclohexenone dissolved in ethanol was continuously administered to four of the mature sheep via rumeral cannulal at the rate of 2.0, 5.0, 7.0 and 10.0 mg/kg/day in acetone at one milliliter per hour for 24 hours using the method described in Teel, P.D., et al, "continuous administration of famphur for control of ticks and bed bugs feeding on rumenants," J. Econ. Entomol, 70:664–666. The two remaining sheep were untreated controls. The control animals received ethanol only. The four treatment and two control sheep where challenged with 20 pairs of adults and 100 larvae of American dog tick (*Dermacentor variabilis*), (*Amblyomma maculatum*) and lone star tick (*Amblyomma americanum*). Following a 72 hour attachment period for adults and 48 hours for nymphs attachment was determined and nonattached ticks were removed. The attached ticks and nymphs were allowed to feed. Parameters on tick, repletion, molt and fecundity were determined on total numbers of nymphs and adults attached. The results of these tests are set forth in Table I, II and III, hereinbelow.

TABLE I

Mean effects of 3-(2-ethylhexanoyloxy)-5,5-dimethyl-2-(2',4'-dimethylphenyl)-2-cyclohexenone to *Amblyomma americanum* (L.) feeding on sheep receiving the compound at 4 rates via rumen infusion

| Parameter | Dosage rate (mg/kg/day) | | | | |
|---|---|---|---|---|---|
| | 2.0 | 5.0 | 7.0 | 10.0 | Control |
| % Adult female repletion | 100.0 | 100.0 | 90.0 | 100.0 | 97.4 |
| % Adult female mortality | 5.2 | 0.0 | 5.0 | 5.0 | 7.7 |
| Repletion wt. (g) | 0.91 | 0.91 | 0.61 | 0.74 | 0.90 |
| Egg mass wt. (g) | 0.53 | 0.56 | 0.27 | 0.44 | 0.51 |
| % Hatch | 74.7 | 88.9 | 11.4 | 82.4 | 86.7 |
| Estimated larvae produced (EL) | 7924.2 | 9880.3 | 613.8 | 7210.0 | 8836.5 |
| % Nymph repletion | 22.2 | 100.0 | 100.0 | 77.7 | 100.0 |
| % Nymph mortality | —[a] | 0.0 | 89.3 | 71.4 | 2.8 |
| % Nymphal molt | — | 100.0 | 53.8 | 100.0 | 97.2 |
| Estimated cumulative control (ECC) | — | 0.0 | 96.2 | 36.6 | — |

[a]Inadequate sample size due to poor attachment.

TABLE II

Means effects of 3-(2-ethylhexanoyloxy)-5,5-dimethyl-2-(2',4'-dimethylphenyl)-2-cyclohexenone to *Amblyomma maculatum* Koch feeding on sheep receiving the experimental compound at 4 rates via rumen infusion.

| Parameter | Dosage rate (mg/kg/day) | | | | |
|---|---|---|---|---|---|
| | 2.0 | 5.0 | 7.0 | 10.0 | Control |
| % Adult female repletion | 89.4 | 88.0 | 33.3 | 24.0 | 92.6 |
| % Adult female mortality | 5.2 | 5.8 | 8.3 | 4.0 | 0.0 |
| Repletion wt. (g) | 0.93 | 1.02 | 0.76 | 0.88 | 0.92 |
| Egg mass wt. (g) | 0.54 | 0.50 | 0.03 | 0.29 | 0.50 |
| % Hatch | 10.7 | 46.6 | 0.4 | 0.0 | 72.3 |
| Estimated larvae produced (EL) | 1163.1 | 4694.5 | 2.8 | 0.0 | 7192.4 |
| % Nymph repletion | 100.0 | 100.0 | 100.0 | 100.0 | 100.0 |
| % Nymphal mortality | 0.0 | 0.0 | 39.0 | 1.9 | 0.0 |
| % Nymphal molt | 100.0 | 97.5 | 92.7 | 100.0 | 100.0 |
| Estimated cumulative control (ECC) | 84.6 | 60.0 | 100.0 | 100.0 | — |

TABLE III

Mean effects of 3-(2-ethylhexanoyloxy)-5,5-dimethyl-2-(2',4'-dimethylphenyl)-2-cyclohexenone to *Dermacentor variabilis* (Say) feeding on sheep receiving the exerimental compound at 4 rates via rumen infusion.

| Parameter | Dossage rate (mg/kg/day) | | | | |
|---|---|---|---|---|---|
| | 2.0 | 5.0 | 7.0 | 10.0 | Control |
| % Adult female repletion | 100.0 | 100.0 | 75.0 | 100.0 | 100.0 |
| % Adult female mortality | 0.0 | 27.3 | 79.1 | 94.7 | 0.0 |
| Repletion wt. (g) | 0.50 | 0.32 | 0.27 | 0.39 | 0.40 |
| Egg mass wt. (g) | 0.28 | 0.07 | 0.01 | 0.03 | 0.24 |
| % Hatch | 21.4 | 0.9 | 0.0 | 0.0 | 93.7 |
| Estimated larvae produced (EL) | 1208.7 | 13.3 | 0.0 | 0.0 | 4463.9 |
| % Nymph repletion | 100.0 | 100.0 | 100.0 | 100.0 | 100.0 |
| % Nymph mortality | 34.7 | 6.6 | 86.9 | 85.9 | 5.9 |
| % Nymph molt | 88.4 | 96.4 | 21.3 | 29.7 | 93.7 |
| Estimated cumulative control (EEC) | 74.4 | 100.0 | 100.0 | 100.0 | — |

RESULTS AND DISCUSSION

Tables I to III summarize data collected at the 2.0, 5.0, 7.0 and 10.0 mg/kg/day rates for each tick species. 3-(2-ethylhexanoyloxy)-5,5-dimethyl-2(2',4'-dimethylphenyl)-2-cyclohexenone was most effective against *D. variabilis*, followed by *A. maculatum*, and least effective against *A. americanum*. The test compound was effective against all three test species at 7.0 mg/kg/day.

3-(2-Ethylhexanoyloxy)-5,5-dimethyl-2(2',4'-dimethylphenyl)-2-cyclohexenone demonstrates its greatest effectiveness against *A. americanum at* 7 mg/kg/day as is reflected in the lowest average repletion weight, egg mass weight and % hatch at this rate (Table I). Nympth mortality and molt position, and a prominent dose-response relationship was observed. Dying replete femals slowly turned black in color and ova were not produced. This dose-response relationship was also evident in the weight of replete femals, ova produced, and % hatch.

What appeared to be fully developed larvae were observed within the egg case of significant portions of egg masses from surviving femals fed on treated sheep, however, eclosion did not occur. This was not observed among control egg masses. The EL values for 3-(2-ethylhexanoyloxy)-5,5-dimethyl-2-(2',4'-dimethylphenyl)-2-cyclohexenone reflect these total effects. Nymph mortality and molting ability show the same trend toward increased dosage, although it is not as sharply delineated. Replete nymphs were observed to turn black in color and succumb before molting, and mortality among newly molted adults increased with dosage rate. The estimated cumulative control based on adult and nymph data was 100% at the 5.0, 7.0 and 10.0 mg/kg/day rates. Clinical signs of toxicity to sheep were not observed for 3-(2-ethylhexanoyloxy)-5,5-dimethyl-2-(2',4'-dimethylphenyl)-2-cyclohexenone at these rates.

It will be understood that the Acarina ectoparasitic species employed in the above tests are representative of a wide variety of ectoparasites that can be controlled by the methods of this invention. The method of this invention is useful for the control of ectoparasitic species belonging to the order Acarina both on and in warm-blooded animals. Representative of such ecoparasites are mites that belong to the family Demodicidae, such as the hog follicle mite (*Demodex phylloides*), the dog follicle mite (*Demodex cania*) and the cattle follicle mite (*Demodex bovis*) and the like; the family Sarcoptidae, such as the itch or mange mite (*Sarcoptes scabiei*) and the scaly-leg mite (*Knemidocoptes mutans*); the family Psoroptidae, such as scab mite (*Psoroptes equi*) and sheep scab mite (*Psoroptes ovis*); and the family Trombiculidae such as chigger mites (*Trombicula irritans*). Other Acarina ectoparasital ticks can be controlled by the process of this invention. Representative of these ectoparasites are tick species belonging to the family *Ixodidae* such as cattle tick, *Boophilus annulatus;* and the Rocky Mountain Wood tick (*Dermacentor andersoni*); and tick species belonging to the family *Argasidae*, and fowl tick (*Argas persicus*).

The method of this invention can be used to control Acarina ectoparasite species on warm-blooded animals. Representative of such warm-blooded animals that can be so treated are horses, dogs, cats, cattle, sheep, goats, hogs and the like. The method of this invention may also be used to control certain Acarina ectoparasite species that affect humans.

The compounds utilized the active toxicant in the method of this invention in some instances, be orally administered directly in an undiluted form of the animal to be treated or the active compound may be formulated with a suitable carrier into a composition prior to all. By the term, "suitable" is meant that the carrier is chosen, having regard to the active compound employed and the animal being treated so that it will not have any deleterious effect upon the animal being treated, the method of this invention or the results obtained thereby. The composition can be a solid or a liquid, depending on how the composition is to be applied.

It is believed to be within the competence of of one skilled in the art to choose the appropriate carrier for a particular compound and a particular application.

Suitable liquid carriers include, water, N-methylpyrrolidone or other non-toxic liquid carriers known to those skilled in the art. The liquid carrier may be used with or without surface active agents. Liquid concentrates may be prepared by dissolving one of the active compounds with a liquid carrier that is non-toxic to mammals and the like, and dispersing the active toxicant in water with the aid of suitable surface active emulsifying and dispersing agents.

The choice of dispersing and emulsifying agents and the amount employed is dictated by the value of the composition and the ability of the agent to facilitate the dispersion of the toxicant. Generally, it is desirable to use as little of the agent as is possible. Nonionic, anionic, amphoteric or cationic dispersing and emulsifying agents may be employed. Illustrative of useful dispersing and emulsifying agents are the condensation products of alkylene oxides with phenol and organic acids, alkyl aryl sulfonates, complex ether alcohols, quaternary ammonium compounds and the like.

The active compound may also be formulated in solid form, such as a tablet, a gel, a cream or the like. In the preparation of solid formulations, the active compound is dispersed in and on non-toxic solid materials such as potato starch, lactose, sucrose, corn starch, vaseline, propylene, glycol, parafin, glycerin, formal and the like.

Compositions useful in the conduct of the method of this invention may also contain optional ingredients insofar as they do not interfere with the activity of the compounds toward the Acarina ectoparasite. Other optional ingredients include medicaments, bactericides, vitamins and the like.

The precise amount of the active compound used will, of course, depend upon a number of factors, including the specific compound employed, the degree of infestation, the internal deviation of treatment, the size and species of the affected animal and the like. However, in general, the amount of the active compound used will range from about 2.0 to about 7.0 milligrams of active compound per kilogram of animal body weight per day.

What is claimed is:

1. A method of controlling ectoparasitic species of the order Acarina in warm-blooded animals which comprises orally administering to said animal an ectoparasitically effective amount of a compound of the formula:

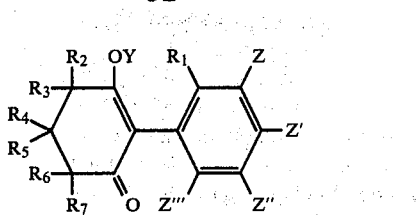

wherein:

Z, Z', Z" and Z'" are individually hydrogen, haloalkyl, halogen, alkyl, polyhaloalkyl, alkoxy, cyano, nitro, alkylthio, alkanoyl, amido, amino, alkylsulfonyl or alkylsulfinyl substituents;

Y is hydrogen or

wherein:

R is hydrogen, halogen, alkyl, alkenyl, alkynyl, bicycloalkyl, bicyloalkenyl, cycloalkyl, cycloalkenyl, phenyl, phenylalkyl, naphthyl or naphthylalkyl all of which except hydrogen and halogen may be substituted with one or more alkyl, cyano, nitro, alkoxy, halogen, haloalkyl, alkoxyalkyl, alkylthio, alkylsulfinyl, alkylsulfonyl, alkylsulfinylalkyl, alkylsulfonylalkyl, alkylthioalkyl or dialkylamino substituent; phenyl wherein the permissible substituents are one or more alkyl, cyano, halogen, nitro, alkoxy, alkylthio, alkylsulfinyl, alkylsulfonyl or dialkylamino substituents; or any two, $R_2$, $R_3$, $R_4$, $R_5$, $R_6$, or $R_7$ substituents together may form an alkylene or alkenylene chain having from 2 to 20 carbon atoms completing a 3, 4, 5, 6 or 7 membered ring structure;

with the proviso that $R_1$, $R_2$, $R_3$, $R_4$, $R_5$, $R_6$, $R_7$, Z, Z', Z'" substituents individually may not include more than ten aliphatic carbon atoms and R may not include more than thirty aliphatic carbon atoms.

2. A method according to claim 1 wherein R is linear or branched chain alkyl having from 1 to 30 carbon atoms.

3. A method according to claim 1 wherein $R_1$ is hydrogen.

4. A method according to claim 1 wherein $R_1$ is alkyl or halogen.

5. A method according to claim 1 wherein $R_2$, $R_2$, $R_3$, $R_4$, $R_6$ and $R_7$ are individually hydrogen or alkyl.

6. A method according to claim 1 wherein Z, Z', Z", and Z'" are individually hydrogen, alkyl, cyano, alkoxy, halogen or trihalomethyl.

7. A method according to claim 1 wherein:
Z, Z', Z" and Z'" are individually hydrogen, alkoxy, alkyl, cyano, halogen or trihalomethyl;
R is a hydrogen or linear or branched chain alkyl having from 1 to 30 carbon atoms;
$R_1$ is alkyl or halogen;
$R_3$, $R_4$, $R_5$, $R_6$, $R_7$ and $R_8$ are individually hydrogen or alkyl.

8. A method according to claim 1 wherein the compound is 3-(2-ethylhexanoyloxy)-5,5-dimethyl-2-(2',4'-dimethylphenyl)-2-cyclohexenone.

9. A method according to claim 1 wherein the compound is 3-(2-ethylhexanoyloxy)-5,5-dimethyl-2-(2'-methylphenyl)-2-cyclohexenone.

10. A method according to claim 1 wherein the compound is (2',4'-dimethylphenyl)-5,5-dimethyl-2-cyclohexanedione.

11. A method according to claim 1 wherein the compound is (2'-methylphenyl)-5,5-dimethyl-2-cyclohexanedione.

* * * * *

UNITED STATES PATENT AND TRADEMARK OFFICE
CERTIFICATE OF CORRECTION

PATENT NO. : 4,175,135
DATED : November 20, 1979
INVENTOR(S) : Robert G. Haines

Page 1 of 2

It is certified that error appears in the above—identified patent and that said Letters Patent is hereby corrected as shown below:

Column 8, line 8, "Sufficiently to contro Dcarma" should read -- sufficient to control Acarina -- .

Column 11, line 15, "$R_6$" of second benzene ring should read -- $R_1$ -- .

Column 18, line 16, "stipped" should read -- stripped -- .

Column 21, line 29, "6-(2',5=-dimethyl-" should read -- 6-(2',5'-dimethyl- -- .

Column 24, lines 14-15, "2-(2',5'-dimethylphenyl)-b 5,5" should read -- 2-(2',5'dimethylphenyl)-5,5 -- .

Column 27, line 5, "variabis" should read -- variabilis -- .
Column 27, line 5, "Amblyama" should read -- Amblyomma -- .

UNITED STATES PATENT AND TRADEMARK OFFICE
CERTIFICATE OF CORRECTION

PATENT NO. : 4,175,135
DATED : November 20, 1979
INVENTOR(S) : Robert G. Haines

It is certified that error appears in the above—identified patent and that said Letters Patent is hereby corrected as shown below:

Column 27, line 6, "Amblyamma" should read -- Amblyomma -- .
Column 30, line 3, "form of" should read -- form to -- .
Column 32, Claim 5, "claim 1 wherein $R_2$, $R_2$, $R_3$, $R_4$" should read -- claim 1 wherein $R_2$, $R_3$, $R_4$ -- .

Signed and Sealed this

Fourteenth Day of October 1980

[SEAL]

*Attest:*

SIDNEY A. DIAMOND

*Attesting Officer*  *Commissioner of Patents and Trademarks*

UNITED STATES PATENT OFFICE
CERTIFICATE OF CORRECTION

Patent No. 4,175,135                    Dated November 20, 1979

Inventor(s)  ROBERT G. HAINES

It is certified that error appears in the above-identified patent and that said Letters Patent are hereby corrected as shown below:

Claim 1. A method of controlling ectoparasitic species of the order Acarina in warm-blooded animals which comprises orally administering to said animal an ectoparasitically effective amount of a compound of the formula:

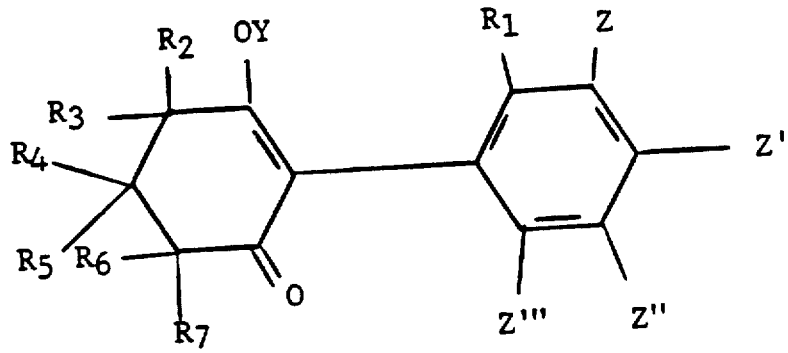

wherein:

Z, Z', Z'' and Z''' are individually hydrogen, haloalkyl, halogen, alkyl, polyhaloalkyl, alkoxy, cyano,

UNITED STATES PATENT OFFICE
CERTIFICATE OF CORRECTION

Patent No. 4,175,135     Dated November 20, 1979

Inventor(s) ROBERT G. HAINES

It is certified that error appears in the above-identified patent and that said Letters Patent are hereby corrected as shown below:

nitro, alkylthio, alkanoyl, amido, amino, alkylsulfonyl or alkylsulfinyl substituents;

Y is hydrogen or $-\overset{\overset{O}{\|}}{C}R$, wherein:

R is hydrogen, halogen, alkyl, alkenyl, alkynyl, bicycloalkyl, bicyloalkenyl, cycloalkyl, cycloalkenyl, phenyl, phenylalkyl, naphthyl or naphthylalkyl all of which except hydrogen and halogen may be substituted with one or more alkyl, cyano, nitro, alkoxy, halogen, haloalkyl, alkoxyalkyl, alkylthio, alkylsulfinyl, alkylsulfonyl, alkylsulfinylalkyl, alkylsulfonylalkyl, alkylthioalkyl or dialkylamino substituent;

$R_1$ is alkyl, polyhaloalkyl or haloalkyl or halogen:

$R_2$, $R_3$, $R_4$, $R_5$, $R_6$ and $R_7$ are individually hydrogen or either substituted or unsubstituted alkyl or phenyl wherein the permissible substituents are one or more alkyl, cyano, halogen, nitro, alkoxy, alkylthio, alkylsulfinyl,

UNITED STATES PATENT OFFICE
CERTIFICATE OF CORRECTION

Patent No. 4,175,135  Dated November 20, 1979

Inventor(s) ROBERT G. HAINES

It is certified that error appears in the above-identified patent and that said Letters Patent are hereby corrected as shown below:

alkylsulfonyl or dialkylamino substituents; or any two $R_2$, $R_3$, $R_4$, $R_5$, $R_6$, or $R_7$ substituents together may form an alkylene or alkenylene chain having from 2 to 20 carbon atoms completing a 3, 4, 5, 6 or 7 membered ring structure;

with the proviso that $R_1$, $R_2$, $R_3$, $R_4$, $R_5$, $R_6$, $R_7$, $Z$, $Z'$, $Z'''$ substituents individually may not include more than ten aliphatic carbon atoms and R may not include more than thirty aliphatic carbon atoms.

Claim 3. After "is"; delete "hydrogen", insert --halogen--.

Signed and Sealed this

Twenty-eighth Day of June 1983

[SEAL]

Attest:

GERALD J. MOSSINGHOFF

Attesting Officer    Commissioner of Patents and Trademarks